US007407807B2

(12) United States Patent
Varsani et al.

(10) Patent No.: US 7,407,807 B2
(45) Date of Patent: Aug. 5, 2008

(54) CHIMAERIC HUMAN PAPILLOMAVIRUS 16 l1 VIRUS LIKE PARTICLES AND A METHOD FOR PREPARING THE PARTICLES

(75) Inventors: Arvind Devshi Varsani, Cape Town (ZA); Edward Peter Rybicki, Cape Town (ZA)

(73) Assignee: University of Cape Town, Cape Town (ZA)

( * ) Notice: Subject to any disclaimer, the term of this patent is extended or adjusted under 35 U.S.C. 154(b) by 258 days.

(21) Appl. No.: 10/514,878

(22) PCT Filed: May 19, 2003

(86) PCT No.: PCT/IB03/01912

§ 371 (c)(1),
(2), (4) Date: Mar. 18, 2005

(87) PCT Pub. No.: WO03/097673

PCT Pub. Date: Nov. 27, 2003

(65) Prior Publication Data

US 2006/0035319 A1 Feb. 16, 2006

(30) Foreign Application Priority Data

May 17, 2002 (ZA) ................................ 2002/3957

(51) Int. Cl.
*A61K 39/12* (2006.01)
*C12N 15/33* (2006.01)
*C12N 15/86* (2006.01)
*A61K 38/00* (2006.01)

(52) U.S. Cl. ................. 435/456; 424/185.1; 435/320.1; 435/235.1

(58) Field of Classification Search ....................... None
See application file for complete search history.

(56) References Cited

U.S. PATENT DOCUMENTS 5,855,891 A * 1/1999 Lowy et al. .............. 424/192.1
6,251,406 B1 * 6/2001 Haefliger et al. ......... 424/258.1

FOREIGN PATENT DOCUMENTS

WO WO 00/09157 2/2000

OTHER PUBLICATIONS

Kimbauer et al. (2001) Papillomavirus L1 major capsid protein self-assembles into virus-like particles that are highly immunogenic, Proc. Natl. Acad. Sci. U S A., vol. 89, No. 24, pp. 12180-12184.*
Mueller, et al., "Chimeric Papillomavirus-like Particles", Virology, United States, vol. 234, No. 1, pp. 93-111, Jul. 21, 1997.
International Search Report (Form PCT/ISA210), 2 pgs., International Application No. PCT/IB03/01912; dated Jan. 5, 2004.

* cited by examiner

*Primary Examiner*—Kathleen Kerr Bragdon
*Assistant Examiner*—Samuel Wei Liu
(74) *Attorney, Agent, or Firm*—Norris McLaughlin & Marcus, PA

(57) ABSTRACT

The invention describes a method for producing a chimaeric human papillomavirus (HPV) L1 polypeptide containing a heterologous peptide, and in particular, a HPV L2 peptide. The method comprises the steps of introducing a DNA sequence coding for the heterologous peptide into a DNA sequence coding for the L1 polypeptide; introducing the DNA sequence including the sequences for the L1 polypeptide and heterologous peptide into a host cell in which the DNA sequence can be expressed; causing expression of the DNA sequence; and recovering the resulting chimaeric L1 polypeptide which includes the heterologous peptide. Typically, the nucleotides encoding the heterologous peptide replace the nucleotides of the L1 polypeptide at the point of insertion. The invention also describes a vector for use in the method, a host cell containing the vector, and a vaccine including the chimaeric HPV L1 polypeptide produced according to the method.

10 Claims, 16 Drawing Sheets

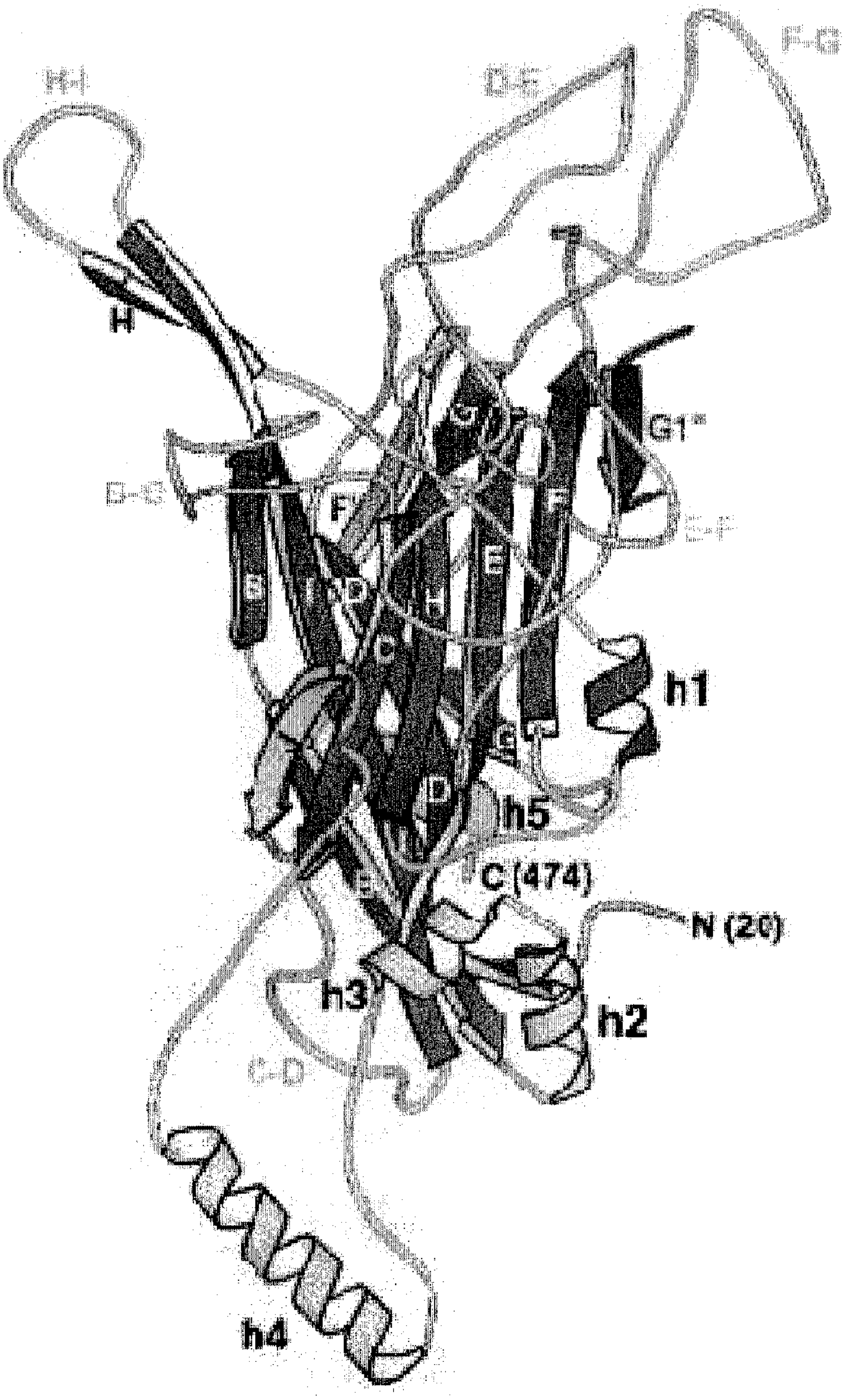
Figure 2 – Prior Art (Chen et al., 2000 and 2001)

```
SEQ  Sa-11: 1518 bp;
Composition   486  A; 293  C; 287  G; 452  T; 0 OTHER
Percentage:   32%  A; 19%  C; 19%  G; 30%  T; 0%OTHER

Molecular Weight (kDa): ssDNA: 468.63    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGT CAGCCATTAG GTGTGGGCAT TAGTGGCCAT
361     CCTTTATTAA ATAAATTGGA TGACACAGAA AATGCTAGTG CTTATGCAGC AAATGCAGGT
421     GTGGATAATA GAGAATGTAT ATCTATGGAT TACAAACAAA CACAATTGTG TTTAATTGGT
481     TGCAAACCAC CTATAGGGGA ACACTGGGGC AAAGGATCCC CATGTACCAA TGTTGCAGTA
541     AATCCAGGTG ATTGTCCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGG CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAGGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAC TAGAAGATAC TTATAGGTTT
1261    GTAACATCCC AGGCAATTGC TTGTCAAAAA CATACACCTC CAGCACCTAA AGAAGATCCC
1321    CTTAAAAAAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCCAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 3 (SEQ ID NO: 2)

```
Translation of Sa-11(1-1518)
Universal code
Total amino acid number: 505, MW=56196
Max ORF: 1-1515, 505 AA, MW=56196

ORIGIN
1       MSLWLPSEAT VYLPPVPVSK VVSTDEYVAR TNIYYHAGTS RLLAVGHPYF PIKKPNNNKI
61      LVPKVSGLQY RVFRIHLPDP NKFGFPDTSF YNPDTQRLVW ACVGVEVGRG QPLGVGISGH
121     PLLNKLDDTE NASAYAANAG VDNRECISMD YKQTQLCLIG CKPPIGEHWG KGSPCTNVAV
181     NPGDCPPLEL INTVIQDGDM VDTGFGAMDF TTLQANKSEV PLDICTSICK YPDYIKMVSE
241     PYGDSLFFYL RREQMFVRHL FNRAGAVGEN VPDDLYIKGS GSTANLASSN YFPTPSGSMV
301     TSDAQIFNKP YWLQRAQGHN NGICWGNQLF VTVVDTTRST NMSLCAAIST SETTYKNTNF
361     KEYLRHGEEY DLQFIFQLCK ITLTADVMTY IHSMNSTILE DWNFGLQPPP GGTLEDTYRF
421     VTSQAIACQK HTPPAPKEDP LKKYTFWEVN LKEKFSADLD QFPLGRKFLL QAGLKAKPKF
481     TLGKRKATPT TSSTSTTAKR KKRKL*
```

Figure 4 (SEQ ID NO: 3)

```
SEQ  Sa-Aopt: 1518 bp;
Composition  486  A; 289  C; 289  G; 454  T; 0 OTHER
Percentage:  32%  A; 19%  C; 19%  G; 30%  T; 0%OTHER

Molecular Weight (kDa): ssDNA: 468.74    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGT CAGCCATTAG GTGTGGGCAT TAGTGGCCAT
361     CCTTTATTAA ATAAATTGGA TGACACAGAA AATGCTAGTG CTTATGCAGC AAATGCAGGT
421     GTGGATAATA GAGAATGTAT ATCTATGGAT TACAAACAAA CACAATTGTG TTTAATTGGT
481     TGCAAACCAC CTATAGGGGA ACACTGGGGC AAAGGATCCT TAGTGGAAGA AACTAGTTTT
541     ATTGATGCTG GTGCACCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGG CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAGGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAC TAGAAGATAC TTATAGGTTT
1261    GTAACATCCC AGGCAATTGC TTGTCAAAAA CATACACCTC CAGCACCTAA AGAAGATCCC
1321    CTTAAAAAAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCCAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 5 (SEQ ID NO: 4)

```
Translation of ChiA(1-1518)
Universal code
Total amino acid number: 505, MW=56288
Max ORF: 1-1515, 505 AA, MW=56288

ORIGIN
1       MSLWLPSEAT VYLPPVPVSK VVSTDEYVAR TNIYYHAGTS RLLAVGHPYF PIKKPNNNKI
61      LVPKVSGLQY RVFRIHLPDP NKFGFPDTSF YNPDTQRLVW ACVGVEVGRG QPLGVGISGH
121     PLLNKLDDTE NASAYAANAG VDNRECISMD YKQTQLCLIG CKPPIGEHWG KGSLVEETSF
181     IDAGAPPLEL INTVIQDGDM VDTGFGAMDF TTLQANKSEV PLDICTSICK YPDYIKMVSE
241     PYGDSLFFYL RREQMFVRHL FNRAGTVGEN VPDDLYIKGS GSTANLASSN YFPTPSGSMV
301     TSDAQIFNKP YWLQRAQGHN NGICWGNQLF VTVVDTTRST NMSLCAAIST SETTYKNTNF
361     KEYLRHGEEY DLQFIFQLCK ITLTADVMTY IHSMNSTILE DWNFGLQPPP GGTLEDTYRF
421     VTSQAIACQK HTPPAPKEDP LKKYTFWEVN LKEKFSADLD QFPLGRKFLL QAGLKAKPKF
481     TLGKRKATPT TSSTSTTAKR KKRKL*
```

Figure 6 (SEQ ID NO: 5)

```
SEQ  Sa-Copt: 1518 bp;
Composition  485  A; 293  C; 286  G; 454  T; 0 OTHER
Percentage:  32%  A; 19%  C; 19%  G; 30%  T; 0%OTHER

Molecular Weight (kDa): ssDNA: 468.59    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGT CAGCCATTAG GTGTGGGCAT TAGTGGCCAT
361     CCTTTATTAA ATAAATTGGA TGACACAGAA TTAGTGGAAG AAACTAGTTT TATTGATGCT
421     GGTGCACCAA GAGAATGTAT ATCTATGGAT TACAAACAAA CACAATTGTG TTTAATTGGT
481     TGCAAACCAC CTATAGGGGA ACACTGGGGC AAAGGATCCC CATGTACCAA TGTTGCAGTA
541     AATCCAGGTG ATTGTCCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGG CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAGGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAC TAGAAGATAC TTATAGGTTT
1261    GTAACATCCC AGGCAATTGC TTGTCAAAAA CATACACCTC CAGCACCTAA AGAAGATCCC
1321    CTTAAAAAAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCCAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 7 (SEQ ID NO: 6)

```
Translation of ChiC(1-1518)
Universal code
Total amino acid number: 505, MW=56337
Max ORF: 1-1515, 505 AA, MW=56337

ORIGIN
1       MSLWLPSEAT VYLPPVPVSK VVSTDEYVAR TNIYYHAGTS RLLAVGHPYF PIKKPNNNKI
61      LVPKVSGLQY RVFRIHLPDP NKFGFPDTSF YNPDTQRLVW ACVGVEVGRG QPLGVGISGH
121     PLLNKLDDTE LVEETSFIDA GAPRECISMD YKQTQLCLIG CKPPIGEHWG KGSPCTNVAV
181     NPGDCPPLEL INTVIQDGDM VDTGFGAMDF TTLQANKSEV PLDICTSICK YPDYIKMVSE
241     PYGDSLFFYL RREQMFVRHL FNRAGTVGEN VPDDLYIKGS GSTANLASSN YFPTPSGSMV
301     TSDAQIFNKP YWLQRAQGHN NGICWGNQLF VTVVDTTRST NMSLCAAIST SETTYKNTNF
361     KEYLRHGEEY DLQFIFQLCK ITLTADVMTY IHSMNSTILE DWNFGLQPPP GGTLEDTYRF
421     VTSQAIACQK HTPPAPKEDP LKKYTFWEVN LKEKFSADLD QFPLGRKFLL QAGLKAKPKF
481     TLGKRKATPT TSSTSTTAKR KKRKL*
```

Figure 8 (SEQ ID NO: 7)

```
SEQ  Sa-eopt: 1518 bp;
Composition  480  A; 285  C; 294  G; 459  T; 0 OTHER
Percentage:  32%  A; 19%  C; 19%  G; 30%  T; 0%OTHER

Molecular Weight (kDa): ssDNA: 468.87    dsDNA: 935.7
ORIGIN
1       ATGTCTCTTT GGCTGCCTAG TGAGGCCACT GTCTACTTGC CTCCTGTCCC AGTATCTAAG
61      GTTGTAAGCA CGGATGAATA TGTTGCACGC ACAAACATAT ATTATCATGC AGGGACATCC
121     AGACTACTTG CAGTTGGACA TCCCTATTTT CCTATTAAAA AACCTAACAA TAACAAAATA
181     TTAGTTCCTA AAGTATCAGG ATTACAATAC AGGGTATTTA GAATACATTT ACCTGACCCC
241     AATAAGTTTG GTTTTCCTGA CACCTCATTT TATAATCCAG ATACACAGCG GCTGGTTTGG
301     GCCTGTGTAG GTGTTGAGGT AGGCCGTGGT CAGCCATTAG GTGTGGGCAT TAGTGGCCAT
361     CCTTTATTAA ATAAATTGGA TGACACAGAA AATGCTAGTG CTTATGCAGC AAATGCAGGT
421     GTGGATAATA GAGAATGTAT ATCTATGGAT TACAAACAAA CACAATTGTG TTTAATTGGT
481     TGCAAACCAC CTATAGGGGA ACACTGGGGC AAAGGATCCC CATGTACCAA TGTTGCAGTA
541     AATCCAGGTG ATTGTCCACC ATTAGAGTTA ATAAACACAG TTATTCAGGA TGGTGATATG
601     GTTGATACTG GCTTTGGTGC TATGGACTTT ACTACATTAC AGGCTAACAA AAGTGAAGTT
661     CCACTGGATA TTTGTACATC TATTTGCAAA TATCCAGATT ATATTAAAAT GGTGTCAGAA
721     CCATATGGCG ACAGCTTATT TTTTTATTTA CGGAGGGAAC AAATGTTTGT TAGACATTTA
781     TTTAATAGGG CTGGTACTGT TGGTGAAAAT GTACCAGACG ATTTATACAT TAAAGGCTCT
841     GGGTCTACTG CAAATTTAGC CAGTTCAAAT TATTTTCCTA CACCTAGTGG TTCTATGGTT
901     ACCTCTGATG CCCAAATATT CAATAAACCT TATTGGTTAC AACGAGCACA GGGCCACAAT
961     AATGGCATTT GTTGGGGTAA CCAACTATTT GTTACTGTTG TTGATACTAC ACGCAGTACA
1021    AATATGTCAT TATGTGCTGC CATATCTACT TCAGAAACTA CATATAAAAA TACTAACTTT
1081    AAGGAGTACC TACGACATGG GGAGGAATAT GATTTACAGT TTATTTTTCA ACTGTGCAAA
1141    ATAACCTTAA CTGCAGACGT TATGACATAC ATACATTCTA TGAATTCCAC TATTTTGGAG
1201    GACTGGAATT TTGGTCTACA ACCTCCCCCA GGAGGCACAC TAGAAGATAC TTATAGGTTT
1261    GTAACATCCC AGGCAATTGC TTGTCAAAAA TTAGTGGAAG AAACTAGTTT TATTGATGCT
1321    GGTGCACCAT ACACTTTTTG GGAAGTAAAT TTAAAGGAAA AGTTTTCTGC AGACCTAGAT
1381    CAGTTTCCTT TAGGACGCAA ATTTTTACTA CAAGCAGGAT TGAAGGCCAA ACCAAAATTT
1441    ACATTAGGAA AACGAAAAGC TACACCCACC ACCTCATCTA CCTCTACAAC TGCTAAACGC
1501    AAAAAACGTA AGCTGTAA
```

Figure 9 (SEQ ID NO: 8)

```
Translation of ChiE(1-1518)
Universal code
Total amino acid number: 505, MW=56117
Max ORF: 1-1515, 505 AA, MW=56117

ORIGIN
1       MSLWLPSEAT VYLPPVPVSK VVSTDEYVAR TNIYYHAGTS RLLAVGHPYF PIKKPNNNKI
61      LVPKVSGLQY RVFRIHLPDP NKFGFPDTSF YNPDTQRLVW ACVGVEVGRG QPLGVGISGH
121     PLLNKLDDTE NASAYAANAG VDNRECISMD YKQTQLCLIG CKPPIGEHWG KGSPCTNVAV
181     NPGDCPPLEL INTVIQDGDM VDTGFGAMDF TTLQANKSEV PLDICTSICK YPDYIKMVSE
241     PYGDSLFFYL RREQMFVRHL FNRAGTVGEN VPDDLYIKGS GSTANLASSN YFPTPSGSMV
301     TSDAQIFNKP YWLQRAQGHN NGICWGNQLF VTVVDTTRST NMSLCAAIST SETTYKNTNF
361     KEYLRHGEEY DLQFIFQLCK ITLTADVMTY IHSMNSTILE DWNFGLQPPP GGTLEDTYRF
421     VTSQAIACQK LVEETSFIDA GAPYTFWEVN LKEKFSADLD QFPLGRKFLL QAGLKAKPKF
481     TLGKRKATPT TSSTSTTAKR KKRKL*
```

Figure 10 (SEQ ID NO: 9)

```
SEQ  Sa-Fopt: 1518 bp;
Composition  484  A; 291  C; 290  G; 453  T; 0 OTHER
Percentage:  32%  A; 19%  C; 19%  G; 30%  T; 0%OTHER

Molecular Weight (kDa): ssDNA: 468.71    dsDNA: 935.7
ORIGIN
1      ATGTCTCTTT GGCTGCCTAG TGAGGCCACT GTCTACTTGC CTCCTGTCCC AGTATCTAAG
61     GTTGTAAGCA CGGATGAATA TGTTGCACGC ACAAACATAT ATTATCATGC AGGGACATCC
121    AGACTACTTG CAGTTGGACA TCCCTATTTT CCTATTAAAA AACCTAACAA TAACAAAATA
181    TTAGTTCCTA AAGTATCAGG ATTACAATAC AGGGTATTTA GAATACATTT ACCTGACCCC
241    AATAAGTTTG GTTTTCCTGA CACCTCATTT TATAATCCAG ATACACAGCG GCTGGTTTGG
301    GCCTGTGTAG GTGTTGAGGT AGGCCGTGGT CAGCCATTAG GTGTGGGCAT TAGTGGCCAT
361    CCTTTATTAA ATAAATTGGA TGACACAGAA AATGCTAGTG CTTATGCAGC AAATGCAGGT
421    GTGGATAATA GAGAATGTAT ATCTATGGAT TACAAACAAA CACAATTGTG TTTAATTGGT
481    TGCAAACCAC CTATAGGGGA ACACTGGGGC AAAGGATCCC CATGTACCAA TGTTGCAGTA
541    AATCCAGGTG ATTGTCCACC ATTAGAGTTA ATAAACACAG TTATTCAGGA TGGTGATATG
601    GTTGATACTG GCTTTGGTGC TATGGACTTT ACTACATTAC AGGCTAACAA AAGTGAAGTT
661    CCACTGGATA TTTGTACATC TATTTGCAAA TATCCAGATT ATATTAAAAT GGTGTCAGAA
721    CCATATGGCG ACAGCTTATT TTTTTATTTA CGGAGGGAAC AAATGTTTGT TAGACATTTA
781    TTTAATAGGG CTGGTACTGT TGGTGAAAAT GTACCAGACG ATTTATACAT TAAAGGCTCT
841    GGGTCTACTG CAAATTTAGC CAGTTCAAAT TATTTTCCTA CACCTAGTGG TTCTATGGTT
901    ACCTCTGATG CCCAAATATT CAATAAACCT TATTGGTTAC AACGAGCACA GGGCCACAAT
961    AATGGCATTT GTTGGGGTAA CCAACTATTT GTTACTGTTG TTGATACTAC ACGCAGTACA
1021   AATATGTCAT TATGTGCTGC CATATCTACT TCAGAAACTA CATATAAAAA TACTAACTTT
1081   AAGGAGTACC TACGACATGG GGAGGAATAT GATTTACAGT TTATTTTTCA ACTGTGCAAA
1141   ATAACCTTAA CTGCAGACGT TATGACATAC ATACATTCTA TGAATTCCAC TATTTTGGAG
1201   GACTGGAATT TTGGTCTACA ACCTCCCCCA GGAGGCACAT TAGTGGAAGA AACTAGTTTT
1261   ATTGATGCTG GTGCACCAGC TTGTCAAAAA CATACACCTC CAGCACCTAA AGAAGATCCC
1321   CTTAAAAAAT ACACTTTTTG GGAAGTAAAT TTAAAGGAAA AGTTTTCTGC AGACCTAGAT
1381   CAGTTTCCTT TAGGACGCAA ATTTTTACTA CAAGCAGGAT TGAAGGCCAA ACCAAAATTT
1441   ACATTAGGAA AACGAAAAGC TACACCCACC ACCTCATCTA CCTCTACAAC TGCTAAACGC
1501   AAAAAACGTA AGCTGTAA
```

Figure 11 (SEQ ID NO: 10)

```
Translation of ChiF(1-1518)
Universal code
Total amino acid number: 505, MW=56032
Max ORF: 1-1515, 505 AA, MW=56032

ORIGIN
1      MSLWLPSEAT VYLPPVPVSK VVSTDEYVAR TNIYYHAGTS RLLAVGHPYF PIKKPNNNKI
61     LVPKVSGLQY RVFRIHLPDP NKFGFPDTSF YNPDTQRLVW ACVGVEVGRG QPLGVGISGH
121    PLLNKLDDTE NASAYAANAG VDNRECISMD YKQTQLCLIG CKPPIGEHWG KGSPCTNVAV
181    NPGDCPPLEL INTVIQDGDM VDTGFGAMDF TTLQANKSEV PLDICTSICK YPDYIKMVSE
241    PYGDSLFFYL RREQMFVRHL FNRAGTVGEN VPDDLYIKGS GSTANLASSN YFPTPSGSMV
301    TSDAQIFNKP YWLQRAQGHN NGICWGNQLF VTVVDTTRST NMSLCAAIST SETTYKNTNF
361    KEYLRHGEEY DLQFIFQLCK ITLTADVMTY IHSMNSTILE DWNFGLQPPP GGTLVEETSF
421    IDAGAPACQK HTPPAPKEDP LKKYTFWEVN LKEKFSADLD QFPLGRKFLL QAGLKAKPKF
481    TLGKRKATPT TSSTSTTAKR KKRKL*
```

Figure 12 (SEQ ID NO: 11)

```
SEQ  Sa-hopt: 1518 bp;
Composition  486  A; 290  C; 293  G; 449  T; 0 OTHER
Percentage:  32%  A; 19%  C; 19%  G; 30%  T; 0%OTHER

Molecular Weight (kDa): ssDNA: 468.82    dsDNA: 935.7
ORIGIN
1      ATGTCTCTTT GGCTGCCTAG TGAGGCCACT GTCTACTTGC CTCCTGTCCC AGTATCTAAG
61     GTTGTAAGCA CGGATGAATA TGTTGCACGC ACAAACATAT ATTATCATGC AGGGACATCC
121    AGACTACTTG CAGTTGGACA TCCCTATTTT CCTATTAAAA AACCTAACAA TAACAAAATA
181    TTAGTTCCTA AAGTATCAGG ATTACAATAC AGGGTATTTA GAATACATTT ACCTGACCCC
241    TTAGTGGAAG AAACTAGTTT TATTGATGCT GGTGCACCAG ATACACAGCG GCTGGTTTGG
301    GCCTGTGTAG GTGTTGAGGT AGGCCGTGGT CAGCCATTAG GTGTGGGCAT TAGTGGCCAT
361    CCTTTATTAA ATAAATTGGA TGACACAGAA AATGCTAGTG CTTATGCAGC AAATGCAGGT
421    GTGGATAATA GAGAATGTAT ATCTATGGAT TACAAACAAA CACAATTGTG TTTAATTGGT
481    TGCAAACCAC CTATAGGGGA ACACTGGGGC AAAGGATCCC CATGTACCAA TGTTGCAGTA
541    AATCCAGGTG ATTGTCCACC ATTAGAGTTA ATAAACACAG TTATTCAGGA TGGTGATATG
601    GTTGATACTG GCTTTGGTGC TATGGACTTT ACTACATTAC AGGCTAACAA AAGTGAAGTT
661    CCACTGGATA TTTGTACATC TATTTGCAAA TATCCAGATT ATATTAAAAT GGTGTCAGAA
721    CCATATGGCG ACAGCTTATT TTTTTATTTA CGGAGGGAAC AAATGTTTGT TAGACATTTA
781    TTTAATAGGG CTGGTACTGT TGGTGAAAAT GTACCAGACG ATTTATACAT TAAAGGCTCT
841    GGGTCTACTG CAAATTTAGC CAGTTCAAAT TATTTTCCTA CACCTAGTGG TTCTATGGTT
901    ACCTCTGATG CCCAAATATT CAATAAACCT TATTGGTTAC AACGAGCACA GGGCCACAAT
961    AATGGCATTT GTTGGGGTAA CCAACTATTT GTTACTGTTG TTGATACTAC ACGCAGTACA
1021   AATATGTCAT TATGTGCTGC CATATCTACT TCAGAAACTA CATATAAAAA TACTAACTTT
1081   AAGGAGTACC TACGACATGG GGAGGAATAT GATTTACAGT TTATTTTTCA ACTGTGCAAA
1141   ATAACCTTAA CTGCAGACGT TATGACATAC ATACATTCTA TGAATTCCAC TATTTTGGAG
1201   GACTGGAATT TTGGTCTACA ACCTCCCCCA GGAGGCACAC TAGAAGATAC TTATAGGTTT
1261   GTAACATCCC AGGCAATTGC TTGTCAAAAA CATACACCTC CAGCACCTAA AGAAGATCCC
1321   CTTAAAAAAT ACACTTTTTG GGAAGTAAAT TTAAAGGAAA AGTTTTCTGC AGACCTAGAT
1381   CAGTTTCCTT TAGGACGCAA ATTTTTACTA CAAGCAGGAT TGAAGGCCAA ACCAAAATTT
1441   ACATTAGGAA AACGAAAAGC TACACCCACC ACCTCATCTA CCTCTACAAC TGCTAAACGC
1501   AAAAAACGTA AGCTGTAA
```

Figure 13 (SEQ ID NO: 12)

```
Translation of ChiH(1-1518)
Universal code
Total amino acid number: 505, MW=56041
Max ORF: 1-1515, 505 AA, MW=56041

ORIGIN
1      MSLWLPSEAT VYLPPVPVSK VVSTDEYVAR TNIYYHAGTS RLLAVGHPYF PIKKPNNNKI
61     LVPKVSGLQY RVFRIHLPDP LVEETSFIDA GAPDTQRLVW ACVGVEVGRG QPLGVGISGH
121    PLLNKLDDTE NASAYAANAG VDNRECISMD YKQTQLCLIG CKPPIGEHWG KGSPCTNVAV
181    NPGDCPPLEL INTVIQDGDM VDTGFGAMDF TTLQANKSEV PLDICTSICK YPDYIKMVSE
241    PYGDSLFFYL RREQMFVRHL FNRAGTVGEN VPDDLYIKGS GSTANLASSN YFPTPSGSMV
301    TSDAQIFNKP YWLQRAQGHN NGICWGNQLF VTVVDTTRST NMSLCAAIST SETTYKNTNF
361    KEYLRHGEEY DLQFIFQLCK ITLTADVMTY IHSMNSTILE DWNFGLQPPP GGTLEDTYRF
421    VTSQAIACQK HTPPAPKEDP LKKYTFWEVN LKEKFSADLD QFPLGRKFLL QAGLKAKPKF
481    TLGKRKATPT TSSTSTTAKR KKRKL*
```

Figure 14 (SEQ ID NO: 13)

"Dates" on the horizontal axis indicates "Time after inoculation (weeks)" and 6-Feb is the date of inoculation. "OD" on the vertical axis indicates "Optical Density".

TTAGTGGAAG AAACTAGTTT TATTGATGCT GGTGCACCA

Figure 27 (SEQ ID NO: 14)

LVEETSFIDA GAP

Figure 28 (SEQ ID NO: 1)

CHIMAERIC HUMAN PAPILLOMAVIRUS 16 I1 VIRUS LIKE PARTICLES AND A METHOD FOR PREPARING THE PARTICLES

BACKGROUND OF THE INVENTION

The invention relates to a method for preparing polypeptides, and in particular virus-like particles (VLPs) or capsomers of human papillomavirus.

The papillomaviruses are a group of small DNA viruses, which induce warts and other lesions in a variety of higher vertebrates including humans.

*Papillomaviruses* (PV) are members of the genus *Papillomavirus*, family Papillomaviridae, and contain a double stranded circular DNA genome with a typical size of 7 900 base pairs (Seedorf et al., 1985). All PVs have a similar genomic organisation, with an early gene region encoding proteins involved in DNA replication and cellular transformation, and a late region encoding the viral capsid proteins (FIG. 1). A non-coding region known as the long control region (LCR) contains control elements for transcription and replication.

*Papillomaviruses* encode two viral structural proteins, L1 and L2. The virion contains 360 L1 molecules arranged as 72 capsomers, each of which is a pentamer composed of five L1 molecules (Baker et al., 1991). The ratio of L1 to L2 molecules has been estimated as approximately 30:1 (Doobar et al., 1987), which suggests that each virion would contain approximately twelve L2 molecules. The greater number of L1 molecules per virion has led to L1 being referred to as the 'major' capsid protein and L2 being referred to as the 'minor' capsid protein.

HPV-16 L1 is encoded by a 1.518 kb gene, giving rise to a protein of 504 amino acids. L1 has a molecular weight of 55 to 58 kD (Browne et al., 1988). Domains of L1 are likely to mediate cell binding and to contain antigenic determinants mediating antibody and T cell immune responses to the virus.

Among the genital human papillomaviruses (HPVs), there are low risk HPVs (for example, HPV 6 and HPV 11) that cause genital warts and cervical lesions that usually regress or do not progress to malignancy, and high risk (or oncogenic) genotypes (for example, HPV 16 and HPV 18), which are associated with high-grade cervical lesions and carcinomas. HPVs have also been implicated as the etiological agents in several other anogenital and upper aerodigestive tract cancers (Breitburd et al., 1999). A compelling body of clinical, molecular, experimental and epidemiological evidence has established that certain HPV types are the main cause of cervical cancer (Lowy et al., 1994; IARC, 1995).

HPV 16 is present in most cases of cervical cancer cases and an additional three types (HPV 18, 31 and 45) are present in approximately an additional 30% of cases (IARC, 1999).

Although the incidence of cervical cancer is decreasing in the US, it is the most common malignancy in women in developing countries, with about 500 000 new cases diagnosed each year.

Traditionally most prophylactic vaccines have consisted of live, attenuated virus or formalin inactivated virus. *Papillomavirus* virions are highly immunogenic, inducing high titres (>10 000) of neutralising antibodies when systemically inoculated (Doretzky et al., 1980; Kirnbauer et al., 1991, 1992). However, due to the difficulties and risks involved in generating large quantities of these traditional vaccines there has been great emphasis on the development of viral protein subunit or virus-like particle (VLP) vaccines.

The best candidate protein for a prophylactic vaccine against HPV is the major capsid protein L1, which self-assembles into VLPs (Schiller and Lowy, 2001). These VLPs are very well characterised, and morphologically appear indistinguishable from whole virions (Chen et al., 2001; Rose et al., 1993). Injection of VLPs into experimental animals induces neutralising antibodies (Rose et al., 1998); preliminary human trials of injected VLP vaccines have also shown that these are well tolerated and highly immunogenic, and in the former case, stimulated robust B and T cell responses (Evans et al., 2001; Harro et al., 2001).

An effective, cheap prophylactic vaccine against oncogenic types of mucotropic HPVs could potentially have an impact on the world cancer burden, especially against HPV 16.

A common-neutralizing epitope for HPV types 6 and 16 has been found in the region (aa) 108-120 of the HPV 16 minor capsid protein, L2 (Kawana et al., 1998, 1999). Balb/c mice that were nasally immunised with a synthetic peptide corresponding to the epitope elicited an immune response that resulted in IgA and IgG antibodies cross-reacting with L1/L2 capsids of HPV 6, 16 and 18 (Kawana et al., 2001). Immunisation of rabbits with either of two overlapping peptides derived from the L2 sequence region 94-122 from either Rabbit oral papillomavirus (ROPV) or Cottontail rabbit papillomavirus (CRPV) resulted in sera which reacted to purified cognate L2, specifically recognised L2 in infected cells, and neutralised virus in vitro. Rabbits immunised with CRPV peptides were immune to CRPV challenge (Embers et al., 2002).

The inventors therefore decided to further investigate the presentation of this L2 epitope on chimaeric L1 VLPs as a vaccine in its own right, and as a model for the presentation of other immunogenic peptide sequences.

SUMMARY OF THE INVENTION

According to a first embodiment of the invention, there is provided a method for producing a chimaeric human papillomavirus (HPV) L1 polypeptide containing a HPV L2 peptide, the method comprising the steps of:

- introducing a DNA sequence coding for the L2 peptide into a DNA sequence coding for the L1 polypeptide;
- introducing the DNA sequence including the sequences for the L1 polypeptide and L2 peptide into a host cell in which the DNA sequence can be expressed;
- causing expression of the DNA sequence; and
- recovering the resulting chimaeric L1 polypeptide which includes the L2 peptide.

The HPV L1 polypeptide and/or HPV L2 peptide may be a HPV-16 polypeptide or peptide.

The HPV L2 peptide may have the following amino acid sequence: LVEETSFIDAGAP (SEQ ID NO: 1), or a sequence which is modification or derivative thereof, with the proviso that the modified or derived sequence is a sequence which has at least 80% homology to the sequence of SEQ ID NO: 1 and codes for a peptide which elicits an immunogenic response against HPV.

One or more nucleotides of the L1 DNA sequence may be deleted at the point of introduction of the L2 DNA sequence, and typically the number of nucleotides deleted from the L1 sequence will correspond with the number of L2 nucleotides inserted.

The expression of the protein could either be in a prokaryotic or eukaryotic expression system.

The chimaeric polypeptide may have the amino acid sequence set out in any one of FIGS. 6, 8, 10, 12 and 14 (SEQ ID NOs: 5, 7, 9, 11 and 13), or a sequence which is at least 80% homologous to any one of the sequences set out in SEQ ID NOs: 5, 7, 9, 11 and 13 and which is capable of eliciting an immunogenic response against HPV. The DNA sequence coding for the chimaeric polypeptide may be the DNA sequence as set out in any one of FIGS. 5, 7, 9, 11 and 13 (SEQ ID NOs: 4, 6, 8, 10 and 12), or a sequence having at least 80% homology to any one of these sequences and which codes for a polypeptide capable of eliciting an immunogenic response against HPV.

The chimaeric L1 polypeptide may assemble into virus-like particles and/or capsomers. The virus-like particle or capsomer may be immunogenic.

According to a second embodiment of the invention, there is provided a chimaeric HPV L1 DNA sequence into which the DNA sequence coding for the above HPV L2 peptide has been inserted, the resulting HPV L1 sequence being capable of expressing the HPV L2 peptide.

One or more nucleotides of the L1 DNA sequence at the point of introduction of the L2 DNA sequence may be deleted, and typically the number of nucleotides deleted from the L1 sequence will correspond with the number of L2 nucleotides inserted.

The chimaeric nucleic acid sequence may be a sequence as set out in any one of FIGS. 5, 7, 9, 11 and 13, or a DNA sequence which is a modification or derivative thereof, with the proviso that the modified or derived DNA sequence has at least 80% homology to any one of the sequences of SEQ ID NOs: 4, 6, 8, 10 and 12 and codes for a chimaeric L1 peptide which is capable of eliciting an immunogenic response against HPV.

According to a third embodiment of the invention, there is provided a vector including the nucleic acid sequence described above.

According to a fourth embodiment of the invention, there is provided a host cell including the vector described above.

According to yet a further embodiment of the invention, there is provided a chimaeric HPV L1 polypeptide that includes the above HPV L2 peptide (SEQ ID NO: 1).

The chimaeric polypeptide may be a chimaeric HPV L1 virus-like particle or capsomer.

According to a further embodiment of the invention, there is provided an HPV polypeptide having the amino acid sequence set out in any one of FIGS. 6, 8, 10, 12 and 14 (SEQ ID NOs: 5, 7, 9, 11 and 13), or a sequence which is a modification or derivative thereof, the modification or derivative being a sequence which is at least 80% homologous to any one of the sequences set out in SEQ ID NOs: 5, 7, 9, 11 and 13 and which is capable of eliciting an immunogenic response against HPV.

According to another embodiment of the invention, there is provided a method for producing a chimaeric human papillomavirus (HPV) L1 polypeptide containing a heterologous peptide, the method comprising the steps of:

- introducing a DNA sequence coding for the heterologous peptide into a DNA sequence coding for the L1 polypeptide;
- introducing the DNA sequence including the sequences for the L1 polypeptide and heterologous peptide into a host cell in which the DNA sequence can be expressed;
- causing expression of the DNA sequence; and
- recovering the resulting chimaeric L1 polypeptide which includes the heterologous peptide.

The heterologous peptide sequence may be any other HPV sequence, or may be derived from any antigenic epitope, B-cell or T-cell specific.

One or more nucleotides of the L1 DNA sequence at the point of introduction of the heterologous DNA sequence may be deleted, and typically the number of nucleotides deleted from the L1 sequence will correspond with the number of heterologous nucleotides inserted.

According to yet a further embodiment of the invention, there is provided a vaccine including the chimaeric HPV L1 polypeptide or a DNA sequence coding for the polypeptide, substantially as described above. The vaccine may be for prophylactic or therapeutic treatment of HPV infection, in particular HPV 6, 16 and 18.

Preferably, the vaccine will be capable of inducing an immunogenic response to HPV and to the introduced peptide in a suitable host.

The vaccine may further include a pharmaceutical excipient and/or adjuvant.

DESCRIPTION OF THE DRAWINGS

FIG. 2 shows the monomer structure of HPV 16 L1;

FIG. 3 shows the nucleotide sequence of the native sequence of the HPV 16 L1 gene into which the L2 epitope was inserted to produce the chimaeric constructs of FIGS. 5 to 14 (SEQ ID NO: 2);

FIG. 4 shows the amino acid sequence of FIG. 3 (SEQ ID NO: 3);

FIG. 5 shows the nucleotide sequence of chimaeric construct A (SEQ ID NO: 4);

FIG. 6 shows the amino acid sequence of chimaeric construct A (SEQ ID NO: 5);

FIG. 7 shows the nucleotide sequence of chimaeric construct C (SEQ ID NO: 6);

FIG. 8 shows the amino acid sequence of chimaeric construct C (SEQ ID NO: 7);

FIG. 9 shows the nucleotide sequence of chimaeric construct E (SEQ ID NO: 8);

FIG. 10 shows the amino acid sequence of chimaeric construct E (SEQ ID NO: 9);

FIG. 11 shows the nucleotide sequence of chimaeric construct F (SEQ ID NO: 10);

FIG. 12 shows the amino acid sequence of chimaeric construct F (SEQ ID NO: 11);

FIG. 13 shows the nucleotide sequence of chimaeric construct H (SEQ ID NO: 12);

FIG. 14 shows the amino acid sequence of chimaeric construct H (SEQ ID NO: 13);

FIG. 27 shows the nucleotide sequence of the L2 peptide which was inserted into the L1 sequence (SEQ ID NO: 14); and FIG. 28 shows the amino acid sequence of the L2 peptide which was inserted into the L1 sequence (SEQ ID NO: 1).

DETAILED DESCRIPTION OF AN EMBODIMENT OF THE INVENTION

Design of Chimaeric Constructs

Primers encoding the peptide:

```
LVEETSFIDAGAP          (SEQ ID NO:1)
```

which is a common-neutralising epitope for HPV 6 and 16 in the region (aa) 108-120 of the HPV minor capsid protein, L2, were synthesised.

Synthesis of Chimaeric Constructs

Chimaeric constructs were prepared by PCR with the primers being designed with the 3' end coding for the L2 peptide. The HPV 16 SA-opt L1 gene (FIGS. 3 and 4) cloned in the pSK plasmid vector was used as a template. The following DNA sequence was used to encode the L2 peptide:

```
                                          (SEQ ID NO:14)
5'-TTAGTGGAAGAAACTAGTTTTATTGATGCTGGTGCACCA-3'.
```

The L2 peptide was inserted into the gene by replacing the regions shown in Table 1. This method of replacing the existing nucleotides, rather than merely inserting the L2 nucleotides into the L1 sequence without any replacement, is advantageous in that disturbances of the tertiary structure are kept to a minimum, and the possibility of steric effects or interference with antibody binding to nearby sequences due to extra peptide "loops" is minimised.

Figure 1:
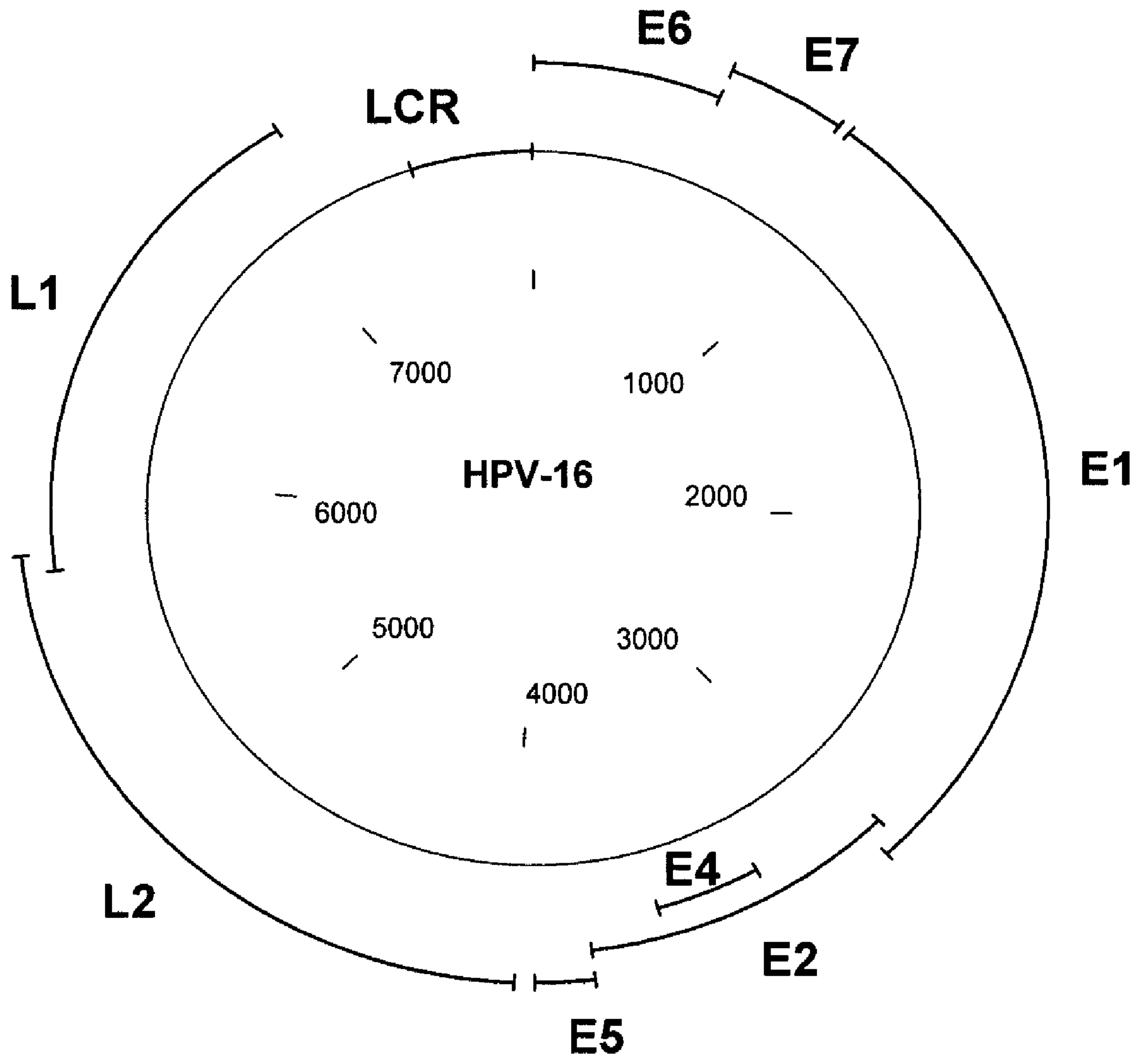
FIG. 1 shows a diagrammatic representation of the genomic organisation of HPV 16.
Figure 15:
FIG. 15 shows a diagrammatic representation of the chimaeric construct A.
Figure 16:
FIG. 16 shows a diagrammatic representation of the chimaeric construct C.
Figure 17:
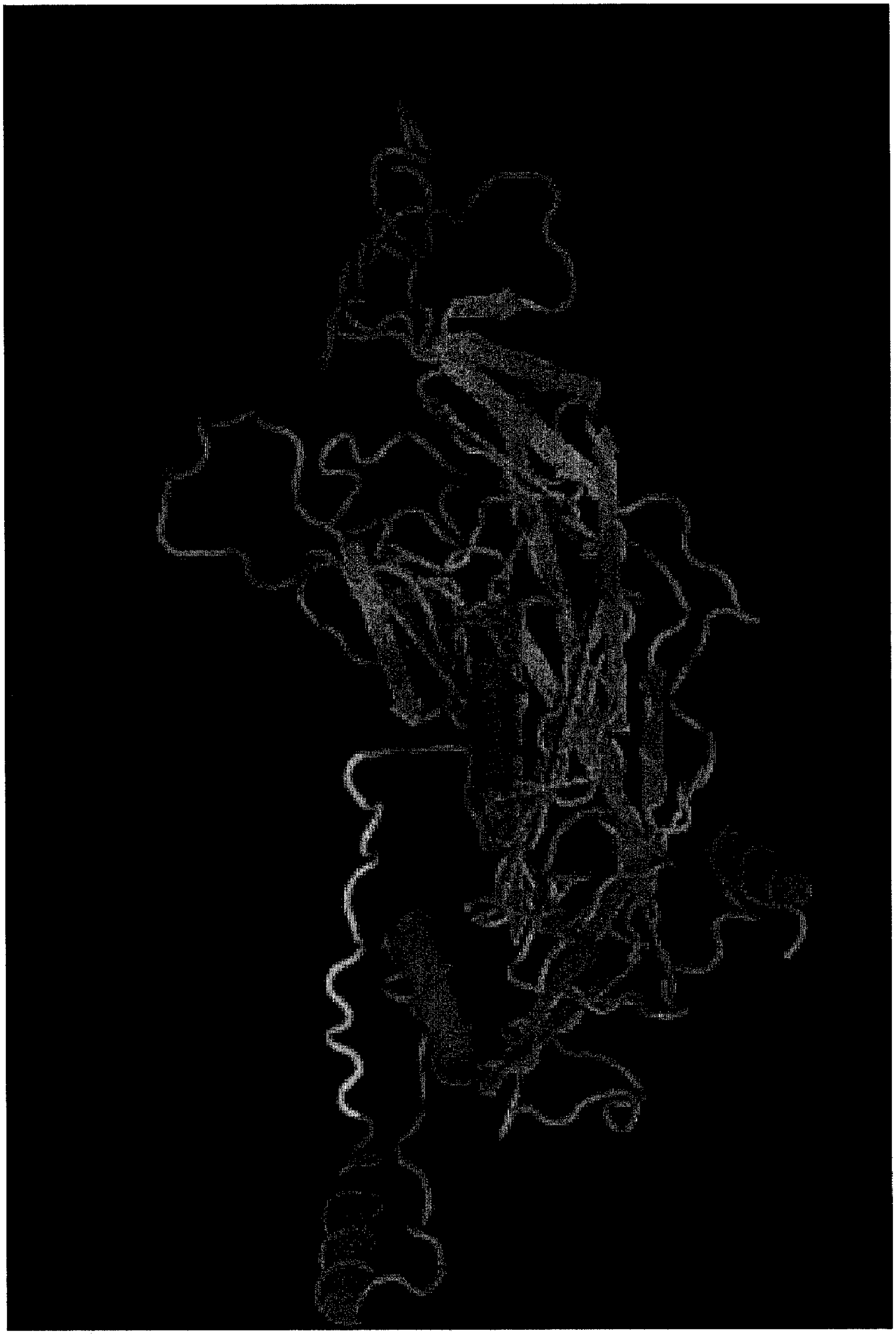
FIG. 17 shows a diagrammatic representation of the chimaeric construct E.
Figure 18:
FIG. 18 shows a diagrammatic representation of the chimaeric construct F.
Figure 19:
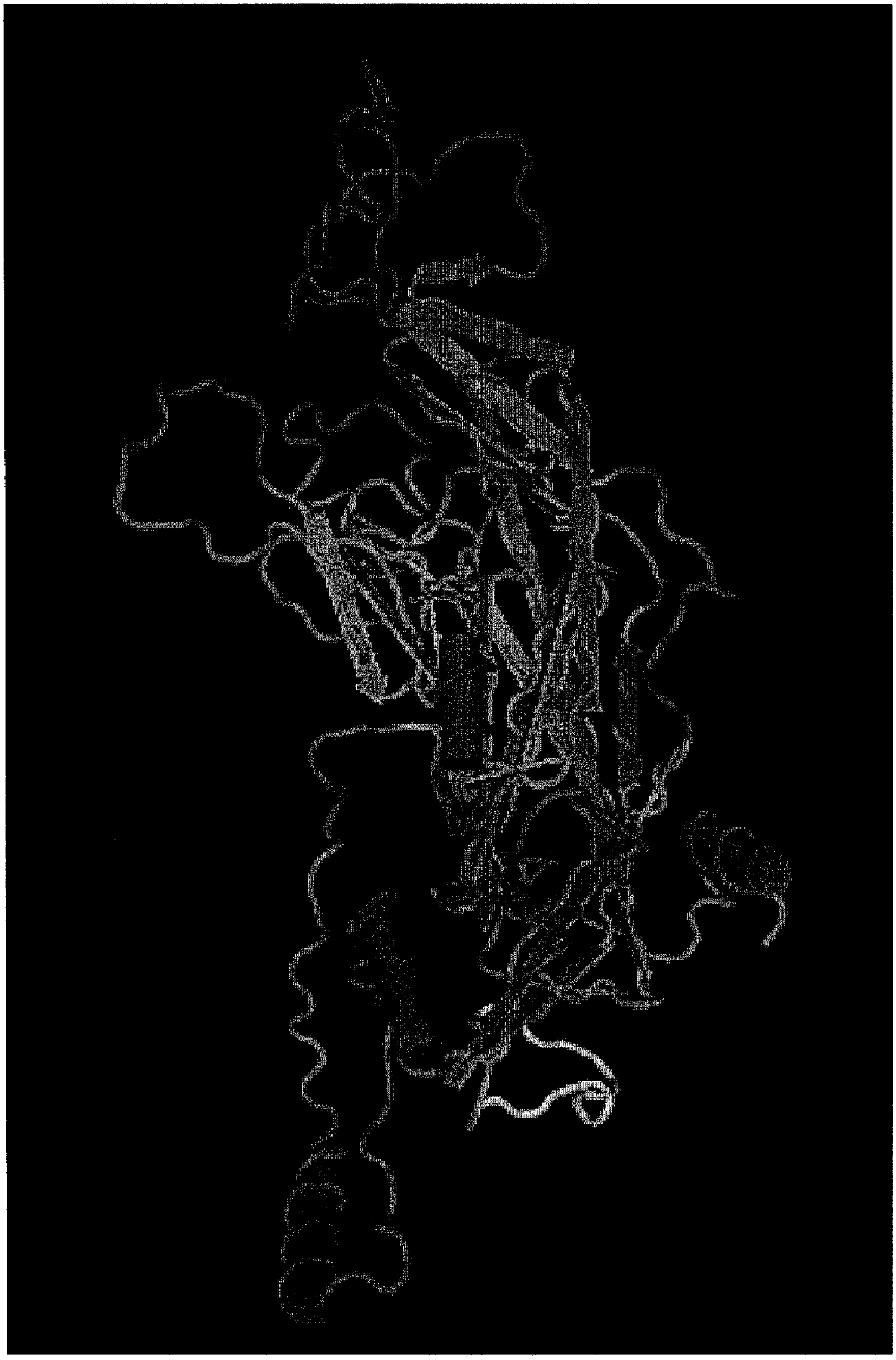
FIG. 19 shows a diagrammatic representation of the chimaeric construct H.

The position of the inserted L2 epitope is depicted for the chimaeric constructs in FIGS. 15 to 19 respectively.

The chimaeric genes from the sequenced pSK constructs were cloned into a pFastbac1 vector (SalI/XbaI site). The DNA from the pFastbac1 clones was used to transfect DH10bac cells to prepare bacmid clones.

The chimaeric constructs were expressed in insect cells using the Bac-to-Bac® baculovirus expression system (Life Technologies).

TABLE 1

Insertion of L2 peptide

| Chimaeric construct | Nucleotide position of L2 peptide | Shown in FIG. No. (SEQ I.D. NO) | Amino acid position of L2 peptide | Shown in FIG. No. (SEQ I.D. NO) |
|---|---|---|---|---|
| A | 520-558 | 5 (4) | 174-186 | 6 (5) |
| C | 391-429 | 7 (6) | 131-143 | 8 (7) |
| E | 1291-1329 | 9 (8) | 431-443 | 10 (9) |
| F | 1240-1278 | 11 (10) | 414-426 | 12 (11) |
| H | 241-279 | 13 (12) | 81-93 | 14 (13) |

According to the HPV 16 L1 monomer structure published by Chen et al. (2000) (FIG. 2), various surface loops and regions are exposed when pentamers and high order structures are formed.

Based on the epitope mapping of the V5 antibody (neutralising antibody raised to L1), various regions/loops were selected for the insertion of the L2 peptide so as to maintain the V5 antibody binding region of the L1 VLPs.

The major antigenic region (V5 binding region) of the L1 molecule has been mapped with amino acid residues A266, (with F50 being located beneath the surface residue V271) and S282 (Roden et al., 1996, White et al., 1999). Based on these residues, the inventors decided not to alter the B loop of the molecule, as this would alter the antigenic region and possibly destroy vital L1 epitopes.

The following L1 regions were therefore selected for insertion of the L2 peptide:

A: E-F loop (SEQ ID NO: 4 and 5)

C: D-E loop (SEQ ID NO: 6 and 7)

E: region between the h4 helix and J region of L1 (SEQ ID NO: 8 and 9)

F: h4 helix (SEQ ID NO: 10 and 11)

H: internal C-D loop (SEQ ID NO: 12 and 13)

The bacmid DNA was transferred into sf21 (Spodoptera frugiperda) insect cells using cellfectin. The basic Bac-to-Bac® protocol was followed to amplify the recombinant virus and infect the sf21 insect cells for expression of the chimaeric VLPs.

A basic HPV 16 L1 VLP purification protocol was followed. The infected insect cells were spun down at 3 000 rpm and resuspended in phosphate buffered saline (PBS) with 0.5M NaCl. The suspension was sonicated 4 times at 5 second intervals. This was then overlayed onto a 40% sucrose cushion and pelleted at 100 000×g for 3 hrs. The pellet was resuspended in CsCl buffer (PBS with 0.4 g/ml CsCl) and resuspended by drawing up through 18 and 26 gauge needles to reduce the viscosity before sonication (4 times at 5 second intervals). The suspension was centrifuged at 100 000×g at 10° C. for 24 hrs.

No distinct bands were observed in CsCl gradients. 500 μl fractions were therefore collected and analysed by ELISA using conformation specific V5 and D9 (linear epitope) monoclonal antibodies. Fractions that were found to react to the V5 and/or D9 antibodies were pooled and dialysed against PBS at 4° C. overnight.

Results

Western blots showed that a polyclonal L2 antibody raised to the peptide in rabbits (obtained from Dr. Neil Christensen of The Jake Gittlen Cancer Research Institute, The Milton S. Hershey Medical Centre, Hersey Pa., USA) bound to the chimaeric L1 particles (55 kD), showing that the L2 epitope is expressed by the chimaeric constructs.

Antibody characterisation of the purified VLPs was carried out by ELISA using a panel of antibodies provided by Dr. Neil Christensen (Chistensen et al., 1996, 2001). Table 2 summarises the data.

TABLE 2

| | V5 | E70 | U4 | 9A | D9 | I23 | L2 |
|---|---|---|---|---|---|---|---|
| A | + | − | + | + | + | + | + |
| C | − | − | + | + | + | + | + |
| E | + | + | + | + | + | + | + |
| F | + | + | + | + | + | + | + |
| H | − | − | − | − | + | + | + |
| SA-opt L1 | + | + | + | + | − | + | − |

A brief description of the antibodies and their binding regions is given in table 3 below.

TABLE 3

| | |
|---|---|
| V5 | Monoclonal, conformation specific antibody; aa 266 and 282 being critical |
| E70 | Monoclonal, conformation specific antibody; aa 50, 266 and 282 being critical |
| U4 | Monoclonal, conformation specific antibody |
| 9A | Monoclonal, binds a linear region in the are aa 1-171 |
| D9 | Monoclonal, binds denatured L1 protein |
| I23 | Monoclonal, binds in the region aa 111-130 |
| L2 | Polyclonal antibody that binding the L2 epitope (aa 108-120) |

Electron Microscopy of the Chimaeric Particles

EM results showed that the particles formed from the chimaeric constructs are not identical to those produced by the wild type HPV L1 gene. The particles formed are mainly in a partially broken down or partially disassembled state and are generally seen to clump together Animal Experimentation with Chimaeric Antigen Six sets of 5 Balb/c mice were used for the animal experimentation to determine if inoculation with the chimaeric VLPs elicited an immune response. Chimaeric VLPs produced from the 5 chimaeric constructs and VLPs produced from a non-chimaeric HPV 16 L1 (SA-opt) were injected at a concentration of 100 μg at two sub-cutaneous sites. The animals were inoculated at weeks 0, 2 and 4. Blood samples and vaginal washes were taken at various time periods.

Figure 20:
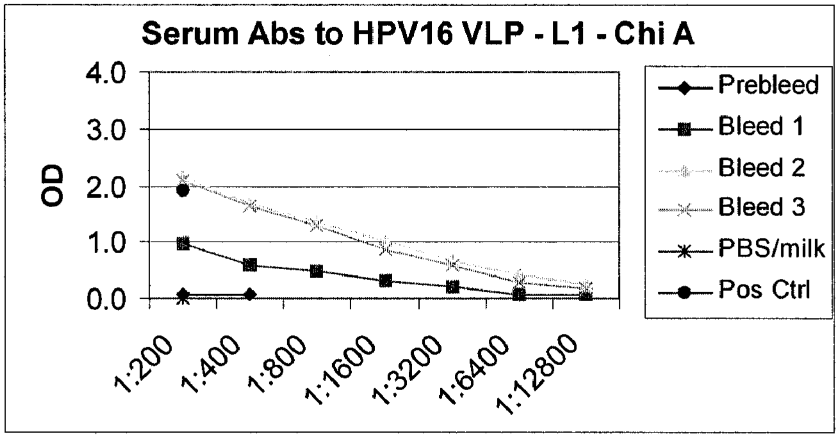
FIG. 20 shows data obtained from end point titrations of mice inoculated with chimaeric VLPs obtained from construct A.
Figure 21:
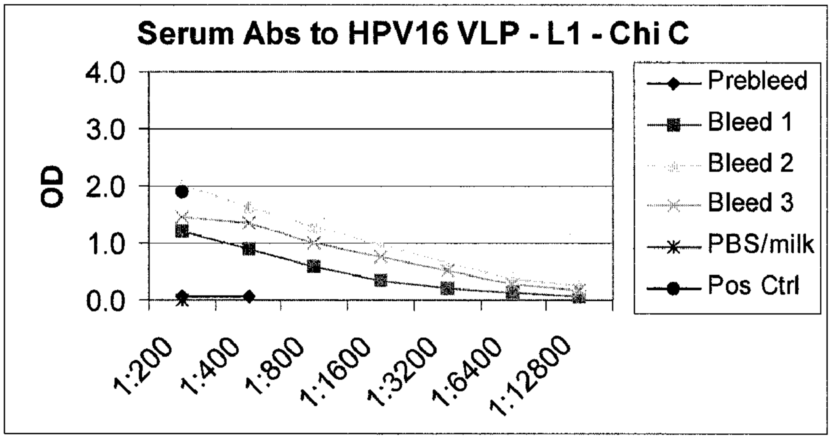
FIG. 21 shows data obtained from end point titrations of mice inoculated with chimaeric VLPs obtained from construct C.
Figure 22:
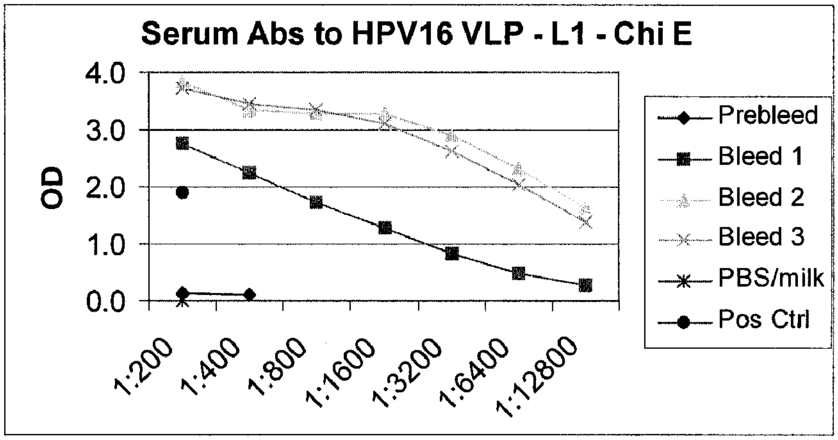
FIG. 22 shows data obtained from end point titrations of mice inoculated with chimaeric VLPs obtained from construct E.
Figure 23:
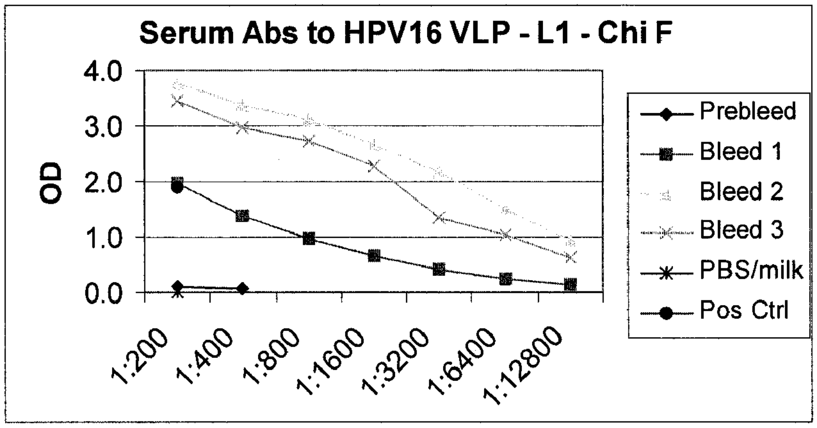
FIG. 23 shows data obtained from end point titrations of mice inoculated with chimaeric VLPs obtained from construct F.
Figure 24:
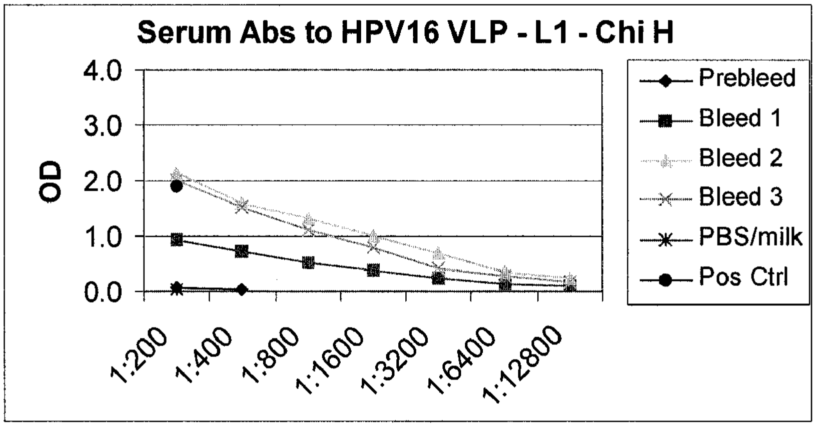
FIG. 24 shows data obtained from end point titrations of mice inoculated with chimaeric VLPs obtained from construct H.
Figure 25:
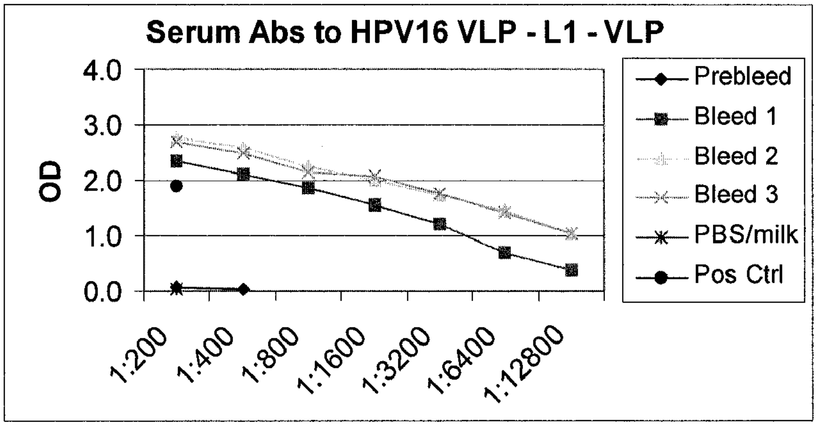
FIG. 25 shows data obtained from end point titrations of mice inoculated with VLPs obtained from a non-chimaeric HPV 16 L1 (SA-opt)
Figure 26:
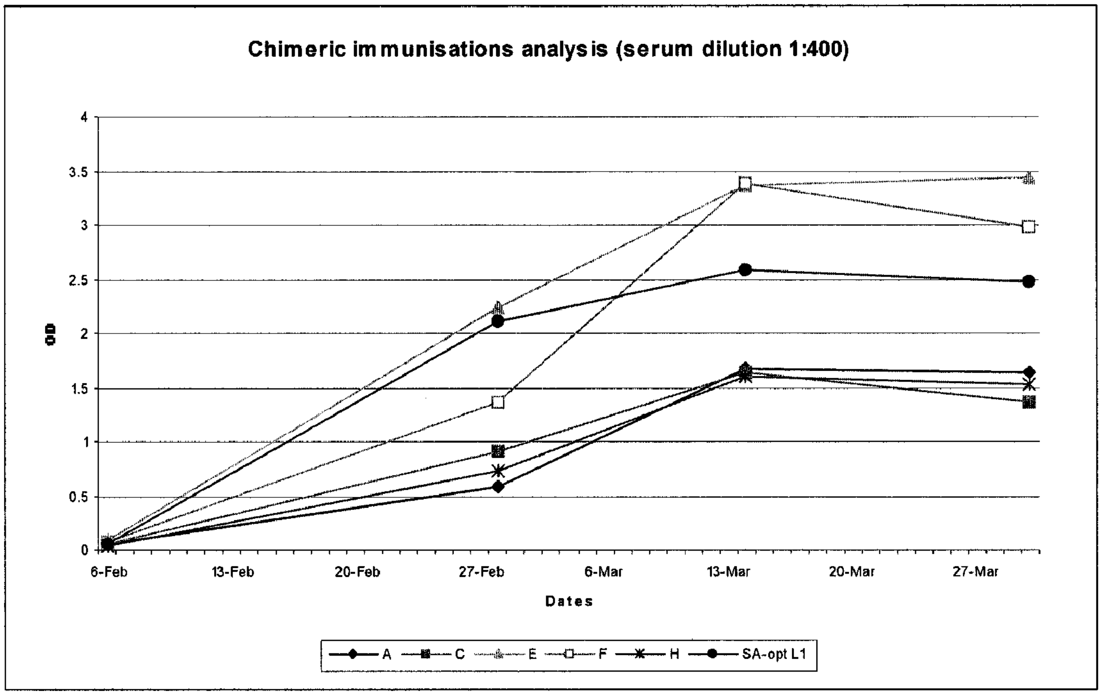
FIG. 26 shows the response of mice to boosters following initial immunisation.

The mouse sera from each group was pooled and analysed by ELISA using VLPs produced in insect cells by recombinant baculoviruses. End point titrations for each group of mice were carried out to determine the extent of the response and give a better reflection of the response (FIGS. 20 to 26).

The results indicate that a high immune response was achieved.

REFERENCES

Baker, T. S., W. W. Newcomb, N. H. Olson, L. M. Cowsert, C. Olson, and J. C. Brown. 1991. Biophys. J. 60:1445-1456.

Breitburd, F. and P. Coursaget. 1999. Cancer Biology 9:431-445.

Browne, H. M., M. J. Churcher, M. A. Stanley, G. L. Smith, and A. C. Minson. 1988. J. Gen. Virol. 69, 1263-1273.

Chen, X. S., Garcea, R. L., Goldberg, I., Casini, G., and Harrison, S. C. (2000). *Mol Cell* 5, 557-567.

Chen, X. S., Casini, G., Harrison, S. C and Garcea, R. (2001). *Journal of Molecular Biology* 307, 173-182.

Christensen, N. D., J. Diller, C. Eklund, J. J. Carter, G. C. Wipf, C. A. Reed, N. M. Cladel, and D. A. Galloway. 1996. Virol. 223, 174-184.

Christensen N D, Cladel N M, Reed C A, Budgeon L R, Embers M E, Skulsky D M, McClements W L, Ludmerer S W, Jansen K U. 2001. 20; 291(2):324-34.

Doorbaar, J., and P. H. Gallimore. 1987. J. Virol. 61:2793-2799.

Doretzky, I., R. Shober, S. K. Chattopadhyay, and D. R. Lowy. 1980. Virology 103:369-375.

M E Embers, L R Budgeon, M Pickel, N D Christensen. 2002. J. Virol., 76 (19): 9798-9805.

Evans, T. G., Bonnez, W., Rose, R. C., Koenig, S., Demeter, L., Suzich, J. A., O'Brien, D., Campbell, M., White, W. I., Balsley, J., and Reichman, R. C. 2001. J Infect. Dis. 183, 1485-1493.

Harro, C. D., Pang, Y. Y., Roden, R. B., Hildesheim, A., Wang, Z., Reynolds, M. J., Mast, T. C., Robinson, R., Murphy, B. R., Karron, R. A., Dillner, J., Schiller, J. T., and Lowy, D. R. 2001. J Natl. Cancer Inst. 93, 284-292.

IARC, World Health Organization. 1995. WHO Report of a technical meeting, Geneva. Ref Type: Report IARC, World Health Organization. 1999. WHO. Report of a technical meeting, Geneva, 16-18 Feb. 1999. 1999. Ref Type: Report Kawana, K., Matsumoto, K., Yoshikawa, H., Taketani, Y., Kawana, T., Yoshiike, K., and Kanda, T. 1998. Virology 245, 353-359.

Kawana, K., Yoshikawa, H., Takentani, Y., Yoshiike, K., and Kanda, T. (1999). *Journal of Virology* 73, 6188-6190.

Kawana, K., Kawana, Y., Yoshikawa, H., Takentani, Y., Yoshiike, K., and Kanda, T. (2001). Vaccine 19, 1496-1502.

Kirnbauer, R., F. Booy, N. Cheng, D. R. Lowy, and J. T. Schiller. 1992. Proc. Natl. Acad. Sci USA. 89, 12180-12184.

Kirnbauer, R., J. Taub, H. Greenstone, R. Roden, M. Durst, L. Gissman, D. R. Lowy, and J. T. Schiller. 1993. J. Virol. 67, 6929-6936.

Lowy, D. R., R. Kirnbauer, and J. T. Schiller. 1994. Proc Natl Acad Sci USA 91:2436-2440.

Roden, R. B. S., H. L. Greenstone, R. Kirnbauer, F. P. Booy, J. Jessie, D. R. Lowy, and J. T. Schiller. 1996. J. Virol. 70, 5875-5883.

Rose, R. C., Bonnez, W., Reichman, R. C., and Garcea, R. L. 1993. J Virol 67, 1936-1944.

Rose, R. C., White, W. I., Li, M., Suzich, J. A., Lane, C., and Garcea, R. L. 1998. Journal of Virology 72, 6151-6154.

Schiller, J. T. and Lowy, D. R. 2001. *Expert. Opin. Biol. Ther.* 1, 571-581.

Seedorf, K., G. Krammer, M. Durst, S. Suhai, and W. G. Röwekamp. 1985. Virol. 145, 181-185.

White, W. I., Wilson, S. D., Palmer-Hill, F. J., Woods, R. M., Ghim, S.-J., Hewitt, L. A., Goldman, D. M., Burke, S. J., Jenson, A. B., Koenig, S., and Suzich, J. A. 1999. J. Virol. 73, 4882-488.

The invention claimed is:

1. A method for producing a chimaeric polypeptide comprising human papillomavirus (HPV) L1 polypeptide containing a heterologous antigenic peptide inserted therein, the method comprising the steps of:

introducing a DNA sequence encoding a heterologous antigenic peptide into a DNA sequence encoding a full-length L1 polypeptide wherein the nucleotides encoding the heterologous antigenic peptide replace a corresponding number of nucleotides within the DNA sequence encoding the L1 polypeptide thereby producing a DNA encoding a chimaeric polypeptide; and wherein said replaced nucleotides within the DNA sequence encoding the L1 polypeptide are: 241-279, 391-429, 520-558, 1240-1278 or 1291-1329 of SEQ ID NOs: 12, 6, 4, 10, and 8, respectively;

introducing the DNA sequence encoding the chimaeric polypeptide into a host cell in which the DNA sequence can be expressed;

causing expression of the DNA sequence; and recovering the produced chimaeric polypeptide.

2. A method according to claim 1, wherein the heterologous antigenic peptide sequence is any HPV peptide sequence which is an antigenic epitope and is B-cell specific or T-cell specific.

3. A method for producing a chimaeric polypeptide comprising human papillomavirus (HPV) L1 polypeptide containing a HPV L2 peptide inserted therein, the method comprising the steps of:

introducing a DNA sequence encoding a common-neutralizing L2 epitopic peptide into a DNA sequence encoding a full-length L1 polypeptide wherein the nucleotides encoding the common-neutralizing L2 epitopic peptide replace a corresponding number of nucleotides within the DNA sequence encoding the L1 polypeptide thereby producing a DNA encoding a chimaeric polypeptide;

introducing the DNA sequence encoding the chimaeric polypeptide into a host cell in which the DNA sequence can be expressed;

causing expression of the DNA sequence;

and recovering the produced chimaeric polypeptide.

4. A method according to claim 3, wherein the HPV L1 polypeptide and/or HPV L2 peptide is/are HPV-16 polypeptide or peptide.

5. A method according to claim 3 wherein the HPV L2 peptide has the amino acid sequence of SEQ ID NO: 1, or a sequence which is a modification or derivative thereof, with the proviso that the modified or derived sequence has at least 80% sequence identity to the sequence of SEQ ID NO: 1 and encodes a peptide capable of eliciting an immunogenic response against HPV.

6. A method according to claim 3, wherein expression of the polypeptide is performed in either a prokaryotic or a eukaryotic expression system.

7. A method according to claim 3, wherein the chimaeric polypeptide has an amino acid sequence set out in any one of SEQ ID NOs:5, 7, 9, 11 and 13, or a sequence which has at least 80% sequence identity to any one of the amino acid sequences set out in SEQ ID NOs:5, 7, 9, 11 and 13 and which is capable of eliciting an immunogenic response against HPV.

8. A method according to claim 3, wherein the DNA sequence encoding the chimaeric polypeptide has a DNA sequence set out in any one of SEQ ID NOs: 4, 6, 8, 10 and 12, or a sequence having at least 80% sequence identity to any one of the nucleotide sequences set out in SEQ ID NOs:4, 6, 8, 10 and 12 and which encodes a chimaeric polypeptide capable of eliciting an immunogenic response against HPV.

9. A method according to claim 3, wherein the chimaeric polypeptide is capable of assembling into virus-like particles and/or capsomers.

10. A method according to claim 9, wherein the virus-like particles or capsomers are immunogenic.

* * * * *

SEQUENCE LISTING

<160> NUMBER OF SEQ ID NOS: 14

<210> SEQ ID NO 1
<211> LENGTH: 13
<212> TYPE: PRT
<213> ORGANISM: Human papillomavirus

<400> SEQUENCE: 1

Leu Val Glu Glu Thr Ser Phe Ile Asp Ala Gly Ala Pro
1 5 10

<210> SEQ ID NO 2
<211> LENGTH: 1518
<212> TYPE: DNA
<213> ORGANISM: Human papillomavirus

<400> SEQUENCE: 2
atgtctcttt ggctgcctag tgaggccact gtctacttgc ctcctgtccc agtatctaag 60
gttgtaagca cggatgaata tgttgcacgc acaaacatat attatcatgc agggacatcc 120
agactacttg cagttggaca tccctatttt cctattaaaa aacctaacaa taacaaaata 180
ttagttccta aagtatcagg attacaatac agggtattta gaatacattt acctgacccc 240
aataagtttg gttttcctga cacctcattt tataatccag atacacagcg gctggtttgg 300
gcctgtgtag gtgttgaggt aggccgtggt cagccattag gtgtgggcat tagtggccat 360
cctttattaa ataaattgga tgacacagaa aatgctagtg cttatgcagc aaatgcaggt 420
gtggataata gagaatgtat atctatggat tacaaacaaa cacaattgtg tttaattggt 480
tgcaaaccac ctatagggga acactggggc aaaggatccc catgtaccaa tgttgcagta 540
aatccaggtg attgtccacc attagagtta ataaacacag ttattcagga tggtgatatg 600
gttgatactg gctttggtgc tatggacttt actacattac aggctaacaa aagtgaagtt 660
ccactggata tttgtacatc tatttgcaaa tatccagatt atattaaaat ggtgtcagaa 720
ccatatggcg acagcttatt tttttattta cggagggaac aaatgtttgt tagacattta 780
tttaataggg ctggtactgt tggtgaaaat gtaccagacg atttatacat taaaggctct 840
gggtctactg caaatttagc cagttcaaat tattttccta cacctagtgg ttctatggtt 900
acctctgatg cccaaatatt caataaacct tattggttac aacgagcaca gggccacaat 960
aatggcattt gttggggtaa ccaactattt gttactgttg ttgatactac acgcagtaca 1020
aatatgtcat tatgtgctgc catatctact tcagaaacta catataaaaa tactaacttt 1080
aaggagtacc tacgacatgg ggaggaatat gatttacagt ttatttttca actgtgcaaa 1140
ataaccttaa ctgcagacgt tatgacatac atacattcta tgaattccac tattttggag 1200
gactggaatt ttggtctaca acctccccca ggaggcacac tagaagatac ttataggttt 1260
gtaacatccc aggcaattgc ttgtcaaaaa catacacctc cagcacctaa agaagatccc 1320
cttaaaaaat acactttttg ggaagtaaat ttaaaggaaa agttttctgc agacctagat 1380
cagtttcctt taggacgcaa atttttacta caagcaggat tgaaggccaa accaaaattt 1440
acattaggaa aacgaaaagc tacacccacc acctcatcta cctctacaac tgctaaacgc 1500
aaaaaacgta agctgtaa 1518

<210> SEQ ID NO 3
<211> LENGTH: 505
<212> TYPE: PRT

-continued

<213> ORGANISM: Human papillomavirus

<400> SEQUENCE: 3

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400
```

-continued

```
Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505


<210> SEQ ID NO 4
<211> LENGTH: 1518
<212> TYPE: DNA
<213> ORGANISM: Human papillomavirus

<400> SEQUENCE: 4

atgtctcttt ggctgcctag tgaggccact gtctacttgc ctcctgtccc agtatctaag     60

gttgtaagca cggatgaata tgttgcacgc acaaacatat attatcatgc agggacatcc    120

agactacttg cagttggaca tccctatttt cctattaaaa aacctaacaa taacaaaata    180

ttagttccta aagtatcagg attacaatac agggtattta gaatacattt acctgacccc    240

aataagtttg gttttcctga cacctcattt tataatccag atacacagcg gctggtttgg    300

gcctgtgtag gtgttgaggt aggccgtggt cagccattag gtgtgggcat tagtggccat    360

cctttattaa ataaattgga tgacacagaa aatgctagtg cttatgcagc aaatgcaggt    420

gtggataata gagaatgtat atctatggat tacaaacaaa cacaattgtg tttaattggt    480

tgcaaaccac ctatagggga acactggggc aaaggatcct tagtggaaga aactagtttt    540

attgatgctg gtgcaccacc attagagtta ataaacacag ttattcagga tggtgatatg    600

gttgatactg gctttggtgc tatggacttt actacattac aggctaacaa aagtgaagtt    660

ccactggata tttgtacatc tatttgcaaa tatccagatt atattaaaat ggtgtcagaa    720

ccatatggcg acagcttatt tttttattta cggagggaac aaatgtttgt tagacattta    780

tttaataggg ctggtactgt tggtgaaaat gtaccagacg atttatacat taaaggctct    840

gggtctactg caaatttagc cagttcaaat tattttccta cacctagtgg ttctatggtt    900

acctctgatg cccaaatatt caataaacct tattggttac aacgagcaca gggccacaat    960

aatggcattt gttggggtaa ccaactattt gttactgttg ttgatactac acgcagtaca   1020

aatatgtcat tatgtgctgc catatctact tcagaaacta catataaaaa tactaacttt   1080

aaggagtacc tacgacatgg ggaggaatat gatttacagt ttattttca actgtgcaaa   1140

ataaccttaa ctgcagacgt tatgacatac atacattcta tgaattccac tattttggag   1200

gactggaatt ttggtctaca acctccccca ggaggcacac tagaagatac ttataggttt   1260

gtaacatccc aggcaattgc ttgtcaaaaa catacacctc cagcacctaa agaagatccc   1320

cttaaaaaat acacttttg ggaagtaaat ttaaaggaaa agttttctgc agacctagat   1380

cagtttcctt taggacgcaa atttttacta caagcaggat tgaaggccaa accaaaattt   1440

acattaggaa aacgaaaagc tacacccacc acctcatcta cctctacaac tgctaaacgc   1500
```

-continued aaaaaacgta agctgtaa 1518

<210> SEQ ID NO 5
<211> LENGTH: 505
<212> TYPE: PRT
<213> ORGANISM: Human papillomavirus

<400> SEQUENCE: 5

Met Ser Leu Trp Leu Pro Ser Glu Ala Thr Val Tyr Leu Pro Pro Val
1 5 10 15

Pro Val Ser Lys Val Val Ser Thr Asp Glu Tyr Val Ala Arg Thr Asn
20 25 30

Ile Tyr Tyr His Ala Gly Thr Ser Arg Leu Leu Ala Val Gly His Pro
35 40 45

Tyr Phe Pro Ile Lys Lys Pro Asn Asn Asn Lys Ile Leu Val Pro Lys
50 55 60

Val Ser Gly Leu Gln Tyr Arg Val Phe Arg Ile His Leu Pro Asp Pro
65 70 75 80

Asn Lys Phe Gly Phe Pro Asp Thr Ser Phe Tyr Asn Pro Asp Thr Gln
85 90 95

Arg Leu Val Trp Ala Cys Val Gly Val Glu Val Gly Arg Gly Gln Pro
100 105 110

Leu Gly Val Gly Ile Ser Gly His Pro Leu Leu Asn Lys Leu Asp Asp
115 120 125

Thr Glu Asn Ala Ser Ala Tyr Ala Ala Asn Ala Gly Val Asp Asn Arg
130 135 140

Glu Cys Ile Ser Met Asp Tyr Lys Gln Thr Gln Leu Cys Leu Ile Gly
145 150 155 160

Cys Lys Pro Pro Ile Gly Glu His Trp Gly Lys Gly Ser Leu Val Glu
165 170 175

Glu Thr Ser Phe Ile Asp Ala Gly Ala Pro Pro Leu Glu Leu Ile Asn
180 185 190

Thr Val Ile Gln Asp Gly Asp Met Val Asp Thr Gly Phe Gly Ala Met
195 200 205

Asp Phe Thr Thr Leu Gln Ala Asn Lys Ser Glu Val Pro Leu Asp Ile
210 215 220

Cys Thr Ser Ile Cys Lys Tyr Pro Asp Tyr Ile Lys Met Val Ser Glu
225 230 235 240

Pro Tyr Gly Asp Ser Leu Phe Phe Tyr Leu Arg Arg Glu Gln Met Phe
245 250 255

Val Arg His Leu Phe Asn Arg Ala Gly Thr Val Gly Glu Asn Val Pro
260 265 270

Asp Asp Leu Tyr Ile Lys Gly Ser Gly Ser Thr Ala Asn Leu Ala Ser
275 280 285

Ser Asn Tyr Phe Pro Thr Pro Ser Gly Ser Met Val Thr Ser Asp Ala
290 295 300

Gln Ile Phe Asn Lys Pro Tyr Trp Leu Gln Arg Ala Gln Gly His Asn
305 310 315 320

Asn Gly Ile Cys Trp Gly Asn Gln Leu Phe Val Thr Val Val Asp Thr
325 330 335

Thr Arg Ser Thr Asn Met Ser Leu Cys Ala Ala Ile Ser Thr Ser Glu
340 345 350

Thr Thr Tyr Lys Asn Thr Asn Phe Lys Glu Tyr Leu Arg His Gly Glu
355 360 365

-continued

```
Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505
```

```
<210> SEQ ID NO 6
<211> LENGTH: 1518
<212> TYPE: DNA
<213> ORGANISM: Human papillomavirus

<400> SEQUENCE: 6

atgtctcttt ggctgcctag tgaggccact gtctacttgc ctcctgtccc agtatctaag     60

gttgtaagca cggatgaata tgttgcacgc acaaacatat attatcatgc agggacatcc    120

agactacttg cagttggaca tccctatttt cctattaaaa aacctaacaa taacaaaata    180

ttagttccta aagtatcagg attacaatac agggtattta gaatacattt acctgacccc    240

aataagtttg gttttcctga cacctcattt tataatccag atacacagcg gctggtttgg    300

gcctgtgtag gtgttgaggt aggccgtggt cagccattag gtgtgggcat tagtggccat    360

cctttattaa ataaattgga tgacacagaa ttagtggaag aaactagttt tattgatgct    420

ggtgcaccaa gagaatgtat atctatggat tacaaacaaa cacaattgtg tttaattggt    480

tgcaaaccac ctatagggga acactggggc aaaggatccc catgtaccaa tgttgcagta    540

aatccaggtg attgtccacc attagagtta ataaacacag ttattcagga tggtgatatg    600

gttgatactg gctttggtgc tatggacttt actacattac aggctaacaa aagtgaagtt    660

ccactggata tttgtacatc tatttgcaaa tatccagatt atattaaaat ggtgtcagaa    720

ccatatggcg acagcttatt tttttattta cggagggaac aaatgtttgt tagacattta    780

tttaataggg ctggtactgt tggtgaaaat gtaccagacg atttatacat taaaggctct    840

gggtctactg caaatttagc cagttcaaat tatttttcta cacctagtgg ttctatggtt    900

acctctgatg cccaaatatt caataaacct tattggttac aacgagcaca gggccacaat    960

aatggcattt gttggggtaa ccaactattt gttactgttg ttgatactac acgcagtaca   1020

aatatgtcat tatgtgctgc catatctact tcagaaacta catataaaaa tactaacttt   1080

aaggagtacc tacgacatgg ggaggaatat gatttacagt ttatttttca actgtgcaaa   1140

ataaccttaa ctgcagacgt tatgacatac atacattcta tgaattccac tattttggag   1200

gactggaatt ttggtctaca acctcccccca ggaggcacac tagaagatac ttataggttt   1260

gtaacatccc aggcaattgc ttgtcaaaaa catacacctc cagcacctaa agaagatccc   1320
```

-continued cttaaaaaat acacttttttg ggaagtaaat ttaaaggaaa agttttctgc agacctagat 1380
cagtttcctt taggacgcaa atttttacta caagcaggat tgaaggccaa accaaaattt 1440
acattaggaa aacgaaaagc tacacccacc acctcatcta cctctacaac tgctaaacgc 1500
aaaaaacgta agctgtaa 1518

<210> SEQ ID NO 7
<211> LENGTH: 505
<212> TYPE: PRT
<213> ORGANISM: Human papillomavirus

<400> SEQUENCE: 7

Met Ser Leu Trp Leu Pro Ser Glu Ala Thr Val Tyr Leu Pro Pro Val
1 5 10 15

Pro Val Ser Lys Val Val Ser Thr Asp Glu Tyr Val Ala Arg Thr Asn
20 25 30

Ile Tyr Tyr His Ala Gly Thr Ser Arg Leu Leu Ala Val Gly His Pro
35 40 45

Tyr Phe Pro Ile Lys Lys Pro Asn Asn Asn Lys Ile Leu Val Pro Lys
50 55 60

Val Ser Gly Leu Gln Tyr Arg Val Phe Arg Ile His Leu Pro Asp Pro
65 70 75 80

Asn Lys Phe Gly Phe Pro Asp Thr Ser Phe Tyr Asn Pro Asp Thr Gln
85 90 95

Arg Leu Val Trp Ala Cys Val Gly Val Glu Val Gly Arg Gly Gln Pro
100 105 110

Leu Gly Val Gly Ile Ser Gly His Pro Leu Leu Asn Lys Leu Asp Asp
115 120 125

Thr Glu Leu Val Glu Glu Thr Ser Phe Ile Asp Ala Gly Ala Pro Arg
130 135 140

Glu Cys Ile Ser Met Asp Tyr Lys Gln Thr Gln Leu Cys Leu Ile Gly
145 150 155 160

Cys Lys Pro Pro Ile Gly Glu His Trp Gly Lys Gly Ser Pro Cys Thr
165 170 175

Asn Val Ala Val Asn Pro Gly Asp Cys Pro Pro Leu Glu Leu Ile Asn
180 185 190

Thr Val Ile Gln Asp Gly Asp Met Val Asp Thr Gly Phe Gly Ala Met
195 200 205

Asp Phe Thr Thr Leu Gln Ala Asn Lys Ser Glu Val Pro Leu Asp Ile
210 215 220

Cys Thr Ser Ile Cys Lys Tyr Pro Asp Tyr Ile Lys Met Val Ser Glu
225 230 235 240

Pro Tyr Gly Asp Ser Leu Phe Phe Tyr Leu Arg Arg Glu Gln Met Phe
245 250 255

Val Arg His Leu Phe Asn Arg Ala Gly Thr Val Gly Glu Asn Val Pro
260 265 270

Asp Asp Leu Tyr Ile Lys Gly Ser Gly Ser Thr Ala Asn Leu Ala Ser
275 280 285

Ser Asn Tyr Phe Pro Thr Pro Ser Gly Ser Met Val Thr Ser Asp Ala
290 295 300

Gln Ile Phe Asn Lys Pro Tyr Trp Leu Gln Arg Ala Gln Gly His Asn
305 310 315 320

Asn Gly Ile Cys Trp Gly Asn Gln Leu Phe Val Thr Val Val Asp Thr
325 330 335

-continued

```
Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505


<210> SEQ ID NO 8
<211> LENGTH: 1518
<212> TYPE: DNA
<213> ORGANISM: Human papillomavirus

<400> SEQUENCE: 8

atgtctcttt ggctgcctag tgaggccact gtctacttgc ctcctgtccc agtatctaag     60

gttgtaagca cggatgaata tgttgcacgc acaaacatat attatcatgc agggacatcc    120

agactacttg cagttggaca tccctatttt cctattaaaa aacctaacaa taacaaaata    180

ttagttccta aagtatcagg attacaatac agggtattta gaatacattt acctgacccc    240

aataagtttg gttttcctga cacctcattt tataatccag atacacagcg gctggtttgg    300

gcctgtgtag gtgttgaggt aggccgtggt cagccattag gtgtgggcat tagtggccat    360

cctttattaa ataaattgga tgacacagaa aatgctagtg cttatgcagc aaatgcaggt    420

gtggataata gagaatgtat atctatggat tacaaacaaa cacaattgtg tttaattggt    480

tgcaaaccac ctatagggga acactggggc aaaggatccc catgtaccaa tgttgcagta    540

aatccaggtg attgtccacc attagagtta ataaacacag ttattcagga tggtgatatg    600

gttgatactg gctttggtgc tatggacttt actacattac aggctaacaa aagtgaagtt    660

ccactggata tttgtacatc tatttgcaaa tatccagatt atattaaaat ggtgtcagaa    720

ccatatggcg acagcttatt tttttattta cggagggaac aaatgtttgt tagacattta    780

tttaataggg ctggtactgt tggtgaaaat gtaccagacg atttatacat taaaggctct    840

gggtctactg caaatttagc cagttcaaat tattttccta cacctagtgg ttctatggtt    900

acctctgatg cccaaatatt caataaacct tattggttac aacgagcaca gggccacaat    960

aatggcattt gttggggtaa ccaactattt gttactgttg ttgatactac acgcagtaca   1020

aatatgtcat tatgtgctgc catatctact tcagaaacta catataaaaa tactaacttt   1080

aaggagtacc tacgacatgg ggaggaatat gatttacagt ttattttca actgtgcaaa   1140
```

-continued

```
ataaccttaa ctgcagacgt tatgacatac atacattcta tgaattccac tattttggag   1200

gactggaatt ttggtctaca acctccccca ggaggcacac tagaagatac ttataggttt   1260

gtaacatccc aggcaattgc ttgtcaaaaa ttagtggaag aaactagttt tattgatgct   1320

ggtgcaccat acactttttg ggaagtaaat ttaaaggaaa agttttctgc agacctagat   1380

cagtttcctt taggacgcaa atttttacta caagcaggat tgaaggccaa accaaaattt   1440

acattaggaa aacgaaaagc tacacccacc acctcatcta cctctacaac tgctaaacgc   1500

aaaaaacgta agctgtaa                                                 1518
```

<210> SEQ ID NO 9
<211> LENGTH: 505
<212> TYPE: PRT
<213> ORGANISM: Human papillomavirus

<400> SEQUENCE: 9

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300
```

-continued

```
Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys Leu Val
            420                 425                 430

Glu Glu Thr Ser Phe Ile Asp Ala Gly Ala Pro Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505
```

<210> SEQ ID NO 10
<211> LENGTH: 1518
<212> TYPE: DNA
<213> ORGANISM: Human papillomavirus

<400> SEQUENCE: 10

```
atgtctcttt ggctgcctag tgaggccact gtctacttgc ctcctgtccc agtatctaag      60

gttgtaagca cggatgaata tgttgcacgc acaaacatat attatcatgc agggacatcc     120

agactacttg cagttggaca tccctatttt cctattaaaa aacctaacaa taacaaaata     180

ttagttccta aagtatcagg attacaatac agggtattta gaatacattt acctgacccc     240

aataagtttg gttttcctga cacctcattt tataatccag atacacagcg gctggtttgg     300

gcctgtgtag gtgttgaggt aggccgtggt cagccattag gtgtgggcat tagtggccat     360

cctttattaa ataaattgga tgacacagaa aatgctagtg cttatgcagc aaatgcaggt     420

gtggataata gagaatgtat atctatggat tacaaacaaa cacaattgtg tttaattggt     480

tgcaaaccac ctatagggga acactggggc aaaggatccc catgtaccaa tgttgcagta     540

aatccaggtg attgtccacc attagagtta ataaacacag ttattcagga tggtgatatg     600

gttgatactg gctttggtgc tatggacttt actacattac aggctaacaa aagtgaagtt     660

ccactggata tttgtacatc tatttgcaaa tatccagatt atattaaaat ggtgtcagaa     720

ccatatggcg acagcttatt tttttattta cggagggaac aaatgtttgt tagacattta     780

tttaataggg ctggtactgt tggtgaaaat gtaccagacg atttatacat taaaggctct     840

gggtctactg caaatttagc cagttcaaat tattttccta cacctagtgg ttctatggtt     900

acctctgatg cccaaatatt caataaacct tattggttac aacgagcaca gggccacaat     960
```

-continued

```
aatggcattt gttggggtaa ccaactattt gttactgttg ttgatactac acgcagtaca   1020

aatatgtcat tatgtgctgc catatctact tcagaaacta catataaaaa tactaacttt   1080

aaggagtacc tacgacatgg ggaggaatat gatttacagt ttatttttca actgtgcaaa   1140

ataaccttaa ctgcagacgt tatgacatac atacattcta tgaattccac tattttggag   1200

gactggaatt ttggtctaca acctccccca ggaggcacat tagtggaaga aactagtttt   1260

attgatgctg gtgcaccagc ttgtcaaaaa catacacctc cagcacctaa agaagatccc   1320

cttaaaaaat acacttttg ggaagtaaat ttaaaggaaa agttttctgc agacctagat    1380

cagtttcctt taggacgcaa atttttacta caagcaggat tgaaggccaa accaaaattt   1440

acattaggaa aacgaaaagc tacacccacc acctcatcta cctctacaac tgctaaacgc   1500

aaaaaacgta agctgtaa                                                 1518
```

```
<210> SEQ ID NO 11
<211> LENGTH: 505
<212> TYPE: PRT
<213> ORGANISM: Human papillomavirus

<400> SEQUENCE: 11

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270
```

-continued

```
Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Val Glu
                405                 410                 415

Glu Thr Ser Phe Ile Asp Ala Gly Ala Pro Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505
```

<210> SEQ ID NO 12
<211> LENGTH: 1518
<212> TYPE: DNA
<213> ORGANISM: Human papillomavirus

<400> SEQUENCE: 12

```
atgtctcttt ggctgcctag tgaggccact gtctacttgc ctcctgtccc agtatctaag     60

gttgtaagca cggatgaata tgttgcacgc acaaacatat attatcatgc agggacatcc    120

agactacttg cagttggaca tccctatttt cctattaaaa aacctaacaa taacaaaata    180

ttagttccta aagtatcagg attacaatac agggtattta gaatacattt acctgacccc    240

ttagtggaag aaactagttt tattgatgct ggtgcaccag atacacagcg gctggtttgg    300

gcctgtgtag gtgttgaggt aggccgtggt cagccattag gtgtgggcat tagtggccat    360

cctttattaa ataaattgga tgacacagaa aatgctagtg cttatgcagc aaatgcaggt    420

gtggataata gagaatgtat atctatggat tacaaacaaa cacaattgtg tttaattggt    480

tgcaaaccac ctatagggga acactggggc aaaggatccc catgtaccaa tgttgcagta    540

aatccaggtg attgtccacc attagagtta ataaacacag ttattcagga tggtgatatg    600

gttgatactg gctttggtgc tatggacttt actacattac aggctaacaa aagtgaagtt    660

ccactggata tttgtacatc tatttgcaaa tatccagatt atattaaaat ggtgtcagaa    720

ccatatggcg acagcttatt tttttattta cggagggaac aaatgtttgt tagacattta    780
```

-continued tttaataggg ctggtactgt tggtgaaaat gtaccagacg atttatacat taaaggctct 840
gggtctactg caaatttagc cagttcaaat tattttccta cacctagtgg ttctatggtt 900
acctctgatg cccaaatatt caataaacct tattggttac aacgagcaca gggccacaat 960
aatggcattt gttggggtaa ccaactattt gttactgttg ttgatactac acgcagtaca 1020
aatatgtcat tatgtgctgc catatctact tcagaaacta catataaaaa tactaacttt 1080
aaggagtacc tacgacatgg ggaggaatat gatttacagt ttatttttca actgtgcaaa 1140
ataaccttaa ctgcagacgt tatgacatac atacattcta tgaattccac tattttggag 1200
gactggaatt ttggtctaca acctccccca ggaggcacac tagaagatac ttataggttt 1260
gtaacatccc aggcaattgc ttgtcaaaaa catacacctc cagcacctaa agaagatccc 1320
cttaaaaaat acactttttg ggaagtaaat ttaaaggaaa agttttctgc agacctagat 1380
cagtttcctt taggacgcaa atttttacta caagcaggat tgaaggccaa accaaaattt 1440
acattaggaa aacgaaaagc tacacccacc acctcatcta cctctacaac tgctaaacgc 1500
aaaaaacgta agctgtaa 1518

<210> SEQ ID NO 13
<211> LENGTH: 505
<212> TYPE: PRT
<213> ORGANISM: Human papillomavirus

<400> SEQUENCE: 13

Met Ser Leu Trp Leu Pro Ser Glu Ala Thr Val Tyr Leu Pro Pro Val
1 5 10 15

Pro Val Ser Lys Val Val Ser Thr Asp Glu Tyr Val Ala Arg Thr Asn
20 25 30

Ile Tyr Tyr His Ala Gly Thr Ser Arg Leu Leu Ala Val Gly His Pro
35 40 45

Tyr Phe Pro Ile Lys Lys Pro Asn Asn Asn Lys Ile Leu Val Pro Lys
50 55 60

Val Ser Gly Leu Gln Tyr Arg Val Phe Arg Ile His Leu Pro Asp Pro
65 70 75 80

Leu Val Glu Glu Thr Ser Phe Ile Asp Ala Gly Ala Pro Asp Thr Gln
85 90 95

Arg Leu Val Trp Ala Cys Val Gly Val Glu Val Gly Arg Gly Gln Pro
100 105 110

Leu Gly Val Gly Ile Ser Gly His Pro Leu Leu Asn Lys Leu Asp Asp
115 120 125

Thr Glu Asn Ala Ser Ala Tyr Ala Ala Asn Ala Gly Val Asp Asn Arg
130 135 140

Glu Cys Ile Ser Met Asp Tyr Lys Gln Thr Gln Leu Cys Leu Ile Gly
145 150 155 160

Cys Lys Pro Pro Ile Gly Glu His Trp Gly Lys Gly Ser Pro Cys Thr
165 170 175

Asn Val Ala Val Asn Pro Gly Asp Cys Pro Pro Leu Glu Leu Ile Asn
180 185 190

Thr Val Ile Gln Asp Gly Asp Met Val Asp Thr Gly Phe Gly Ala Met
195 200 205

Asp Phe Thr Thr Leu Gln Ala Asn Lys Ser Glu Val Pro Leu Asp Ile
210 215 220

Cys Thr Ser Ile Cys Lys Tyr Pro Asp Tyr Ile Lys Met Val Ser Glu
225 230 235 240

-continued

```
Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505


<210> SEQ ID NO 14
<211> LENGTH: 39
<212> TYPE: DNA
<213> ORGANISM: Human papillomavirus

<400> SEQUENCE: 14

ttagtggaag aaactagttt tattgatgct ggtgcacca                        39
```